(12) United States Patent
Wang et al.

(10) Patent No.: US 7,186,666 B2
(45) Date of Patent: Mar. 6, 2007

(54) CATALYTIC SYSTEMS

(75) Inventors: Yi-Feng Wang, Waterford, NY (US);
Peter D. Phelps, Clifton Park, NY (US)

(73) Assignee: Cyclics Corporation, Schenectady, NY (US)

( * ) Notice: Subject to any disclaimer, the term of this patent is extended or adjusted under 35 U.S.C. 154(b) by 0 days.

(21) Appl. No.: 11/091,721

(22) Filed: Mar. 28, 2005

(65) Prior Publication Data

US 2005/0227861 A1 Oct. 13, 2005

Related U.S. Application Data

(62) Division of application No. 10/102,162, filed on Mar. 20, 2002, now Pat. No. 6,906,147.

(51) Int. Cl.
 *B08J 31/38* (2006.01)
(52) U.S. Cl. .................. 502/104; 502/242; 502/350
(58) Field of Classification Search ................ 502/104, 502/242, 350
See application file for complete search history.

(56) References Cited

U.S. PATENT DOCUMENTS

| | | |
|---|---|---|
| 2,628,171 A | 2/1953 | Green |
| 3,018,272 A | 1/1962 | Griffing et al. |
| 3,090,753 A | 5/1963 | Matuszak et al. |
| 3,786,067 A | 1/1974 | Throckmorton et al. |
| 3,964,923 A | 6/1976 | Zetmeir |
| 3,979,354 A | 9/1976 | Dyckman et al. |
| 4,012,460 A | 3/1977 | Takahashi |
| 4,063,009 A | 12/1977 | Ziegler et al. |
| 4,075,319 A | 2/1978 | Dyckman et al. |
| 4,082,709 A | 4/1978 | Dyckman et al. |
| 4,101,600 A | 7/1978 | Zhukov et al. |
| 4,115,468 A | 9/1978 | Antonov et al. |
| 4,118,432 A | 10/1978 | Kabanov et al. |
| 4,129,548 A | 12/1978 | McDonnell |
| 4,165,305 A | 8/1979 | Sundie et al. |
| 4,187,197 A | 2/1980 | Kabanov et al. |
| 4,230,824 A | 10/1980 | Nodelman |
| 4,232,087 A | 11/1980 | Trask |
| 4,233,232 A | 11/1980 | Howarth |
| 4,235,825 A | 11/1980 | Milam |
| 4,341,842 A | 7/1982 | Lampe |
| 4,377,684 A | 3/1983 | Bolon et al. |
| 4,409,266 A | 10/1983 | Wieczorrek et al. |
| 4,461,854 A | 7/1984 | Smith |
| 4,478,963 A | 10/1984 | McGarry |
| 4,518,283 A | 5/1985 | Gebauer et al. |
| 4,520,123 A | 5/1985 | Hall |
| 4,525,565 A | 6/1985 | Laisney et al. |
| 4,535,102 A | 8/1985 | Kusumoto et al. |
| 4,547,531 A | 10/1985 | Waknine |
| 4,559,262 A | 12/1985 | Cogswell et al. |
| 4,568,703 A | 2/1986 | Ashida |
| 4,584,254 A | 4/1986 | Nakayama et al. |
| 4,590,259 A | 5/1986 | Kosky et al. |
| 4,591,624 A | 5/1986 | Hall |
| 4,605,731 A | 8/1986 | Evans et al. |
| 4,616,077 A | 10/1986 | Silva |
| 4,638,077 A | 1/1987 | Brunelle et al. |
| 4,644,053 A | 2/1987 | Brunelle et al. |
| 4,647,633 A | 3/1987 | Kostelnik |
| 4,672,003 A | 6/1987 | Letoffe |
| 4,680,345 A | 7/1987 | Kobayashi et al. |
| 4,725,666 A | 2/1988 | Curatolo et al. |
| 4,727,134 A | 2/1988 | Brunelle et al. |
| 4,740,583 A | 4/1988 | Brunelle et al. |
| 4,757,132 A | 7/1988 | Brunelle et al. |
| 4,785,060 A | 11/1988 | Nagler |
| 4,803,288 A | 2/1989 | Kitamura et al. |
| 4,812,524 A | 3/1989 | Baghdachi |
| 4,816,548 A | 3/1989 | Evans et al. |
| 4,824,595 A | 4/1989 | Richter et al. |
| 4,829,144 A | 5/1989 | Brunelle et al. |
| 4,831,001 A | 5/1989 | Evans et al. |
| 4,845,178 A | 7/1989 | Hostetler et al. |
| 4,852,591 A | 8/1989 | Wisotzki et al. |
| 4,880,848 A | 11/1989 | Ghali |
| 4,888,411 A | 12/1989 | Shannon et al. |
| 4,889,885 A | 12/1989 | Usuki et al. |
| 4,889,903 A | 12/1989 | Baghdachi |

(Continued)

FOREIGN PATENT DOCUMENTS

| | | |
|---|---|---|
| DE | 3607627 | 9/1987 |
| DE | 4034574 A1 | 5/1992 |
| EP | 0000544 B1 | 8/1982 |
| EP | 0153785 A2 | 9/1985 |
| EP | 0216496 A2 | 4/1987 |
| EP | 0153785 B1 | 7/1989 |
| EP | 419254 A2 | 3/1991 |
| EP | 486832 A2 | 5/1992 |
| EP | 264835 B1 | 6/1992 |
| EP | 235741 B1 | 1/1993 |

(Continued)

OTHER PUBLICATIONS

Communication pursuant to Article 96(2) EPC for 03714278.3-2102, Nov. 25, 2004.
"DuPont™ Tyzor® Organic Titanates General Brochure" (2001) E.I. du Pont de Nemours and Company, 12 pages.
Ahjopalo, L. et al. (2000) "Cyclic Oligomers in Saturated Polyesters" Polymer, vol. 41, No. 23, 8283-8290.

(Continued)

*Primary Examiner*—Robert D. Harlan
(74) *Attorney, Agent, or Firm*—Goodwin Procter LLP

(57) ABSTRACT

This invention relates to single-component and multi-component catalytic systems using aryl titanates. Aryl titanate compounds are useful as catalysts and co-catalysts in single-component and multi-component catalytic systems (e.g., for the polymerization of macrocyclic oligoesters and the depolymerization of polyesters). Multi-component catalytic systems using aryl titanates allow increased versatility in applications such as liquid molding.

14 Claims, No Drawings

U.S. PATENT DOCUMENTS

| | | |
|---|---|---|
| 4,900,706 A | 2/1990 | Sasaki et al. |
| 4,904,810 A | 2/1990 | Brunelle et al. |
| 4,909,846 A | 3/1990 | Barfurth et al. |
| 4,927,728 A | 5/1990 | Isoda et al. |
| 4,942,198 A | 7/1990 | Dickerhof et al. |
| 4,980,453 A | 12/1990 | Brunelle et al. |
| 4,992,228 A | 2/1991 | Heck et al. |
| 4,994,541 A | 2/1991 | Dell et al. |
| 4,999,420 A | 3/1991 | Leitz et al. |
| 5,006,637 A | 4/1991 | Guggenheim et al. |
| 5,019,450 A | 5/1991 | Cogswell et al. |
| 5,023,346 A | 6/1991 | Schon et al. |
| 5,039,717 A | 8/1991 | Kawakami et al. |
| 5,039,783 A | 8/1991 | Brunelle et al. |
| 5,051,482 A | 9/1991 | Tepic |
| 5,071,711 A | 12/1991 | Heck et al. |
| 5,095,088 A | 3/1992 | Wang |
| 5,097,008 A | 3/1992 | Krabbenhoft et al. |
| 5,116,900 A | 5/1992 | Flautt et al. |
| 5,124,427 A | 6/1992 | Potter et al. |
| 5,159,024 A | 10/1992 | Brindöpke et al. |
| 5,175,228 A | 12/1992 | Wang et al. |
| 5,191,013 A | 3/1993 | Cook et al. |
| 5,191,038 A | 3/1993 | Krabbenhoft et al. |
| 5,196,055 A | 3/1993 | Lesney et al. |
| 5,202,386 A | 4/1993 | Hogt et al. |
| 5,207,850 A | 5/1993 | Parekh |
| 5,214,158 A | 5/1993 | Brunelle et al. |
| 5,225,129 A | 7/1993 | van den Berg |
| 5,231,161 A | 7/1993 | Brunelle et al. |
| 5,235,018 A | 8/1993 | Potter et al. |
| 5,237,042 A | 8/1993 | Kim et al. |
| 5,241,880 A | 9/1993 | Mizobata et al. |
| RE34,431 E | 11/1993 | Brunelle et al. |
| 5,260,376 A | 11/1993 | Nakahata et al. |
| 5,264,548 A | 11/1993 | Brunelle et al. |
| 5,281,669 A | 1/1994 | Kambour et al. |
| 5,288,837 A | 2/1994 | Munjal et al. |
| 5,300,392 A | 4/1994 | Odell et al. |
| 5,300,393 A | 4/1994 | Odell et al. |
| 5,300,590 A | 4/1994 | Cook et al. |
| 5,302,484 A | 4/1994 | Odell et al. |
| 5,314,779 A | 5/1994 | Odell et al. |
| 5,321,117 A | 6/1994 | Brunelle |
| 5,340,909 A | 8/1994 | Doerr et al. |
| 5,348,985 A | 9/1994 | Pearce et al. |
| 5,349,040 A | 9/1994 | Trinks et al. |
| 5,350,726 A | 9/1994 | Shaffer |
| 5,350,819 A | 9/1994 | Shaffer |
| 5,356,984 A | 10/1994 | Carbone et al. |
| 5,386,037 A | 1/1995 | Takekoshi et al. |
| 5,387,666 A | 2/1995 | Takekoshi et al. |
| 5,389,719 A | 2/1995 | Takekoshi et al. |
| 5,407,984 A | 4/1995 | Brunelle et al. |
| 5,408,001 A | 4/1995 | Nakahata et al. |
| 5,410,014 A | 4/1995 | Haese et al. |
| 5,418,303 A | 5/1995 | Shaffer |
| 5,420,226 A | 5/1995 | Hamer et al. |
| 5,426,156 A | 6/1995 | Bederke et al. |
| 5,434,244 A | 7/1995 | Warner et al. |
| 5,439,996 A | 8/1995 | Baird et al. |
| 5,444,146 A | 8/1995 | Potter et al. |
| 5,446,122 A | 8/1995 | Warner et al. |
| 5,448,001 A | 9/1995 | Baird |
| 5,466,744 A | 11/1995 | Evans et al. |
| 5,498,651 A | 3/1996 | Brunelle |
| 5,506,316 A | 4/1996 | Shaffer |
| 5,506,328 A | 4/1996 | Chandalia et al. |
| 5,508,343 A | 4/1996 | Holley |
| 5,519,108 A | 5/1996 | Yuo et al. |
| 5,525,673 A | 6/1996 | Nakahata et al. |
| 5,527,976 A | 6/1996 | Takekoshi et al. |
| 5,530,052 A | 6/1996 | Takekoshi et al. |
| 5,591,800 A | 1/1997 | Takekoshi et al. |
| 5,605,979 A | 2/1997 | Priddy, Jr. et al. |
| 5,610,260 A | 3/1997 | Schmalstieg et al. |
| 5,637,655 A | 6/1997 | Priddy, Jr. et al. |
| 5,646,306 A | 7/1997 | Elsasser, Jr. |
| 5,648,454 A | 7/1997 | Brunelle |
| 5,654,395 A | 8/1997 | Jackson et al. |
| 5,656,712 A | 8/1997 | Mirossay |
| 5,661,214 A | 8/1997 | Brunelle et al. |
| 5,663,282 A | 9/1997 | Todt et al. |
| 5,668,186 A | 9/1997 | Brunelle et al. |
| 5,693,722 A | 12/1997 | Priddy, Jr. et al. |
| 5,700,888 A | 12/1997 | Hall |
| 5,703,183 A | 12/1997 | Shaffer |
| 5,707,439 A | 1/1998 | Takekoshi et al. |
| 5,710,086 A | 1/1998 | Brunelle et al. |
| 5,756,644 A | 5/1998 | Hodge et al. |
| 5,760,161 A | 6/1998 | Goins, Jr. et al. |
| 5,786,440 A | 7/1998 | Kohler et al. |
| 5,795,423 A | 8/1998 | Johnson |
| 5,830,541 A | 11/1998 | Carswell et al. |
| 5,849,255 A | 12/1998 | Sawyer et al. |
| 5,869,586 A | 2/1999 | Riedel et al. |
| 5,936,029 A | 8/1999 | Hall |
| 5,947,392 A | 9/1999 | Molnar et al. |
| 5,965,686 A | 10/1999 | Blank et al. |
| 5,968,642 A | 10/1999 | Saito |
| 6,074,978 A | 6/2000 | Shaffer |
| 6,078,135 A | 6/2000 | Lee et al. |
| 6,080,834 A | 6/2000 | Putzig et al. |
| 6,121,466 A | 9/2000 | Osterholt et al. |
| 6,124,412 A | 9/2000 | Bin-Taleb et al. |
| 6,147,026 A | 11/2000 | Setiabudi et al. |
| 6,171,995 B1 | 1/2001 | Mühlebach et al. |
| 6,191,318 B1 | 2/2001 | Park et al. |
| 6,211,316 B1 | 4/2001 | Seebach |
| 6,271,317 B1 | 8/2001 | Halasa et al. |
| 6,284,868 B1 | 9/2001 | Geprägs et al. |
| 6,297,330 B1 | 10/2001 | Burch, Jr. et al. |
| 6,353,030 B1 | 3/2002 | Prikoszovich |
| 6,369,157 B1 | 4/2002 | Winckler |
| 6,376,026 B1 | 4/2002 | Correll et al. |
| 6,414,103 B1 | 7/2002 | Correll et al. |
| 6,420,047 B2 | 7/2002 | Winckler et al. |
| 6,420,048 B1 | 7/2002 | Wang |
| 6,432,486 B1 | 8/2002 | Paris et al. |
| 6,436,548 B1 | 8/2002 | Phelps |
| 6,436,549 B1 * | 8/2002 | Wang .................. 428/480 |
| 6,458,972 B1 | 10/2002 | Surburg et al. |
| 6,525,164 B2 | 2/2003 | Faler |
| 6,586,558 B2 | 7/2003 | Schmidt et al. |
| 6,639,009 B2 | 10/2003 | Winckler et al. |
| 6,646,134 B2 | 11/2003 | Brugel |
| 6,670,429 B2 | 12/2003 | Appelman et al. |
| 6,787,632 B2 | 9/2004 | Phelps et al. |
| 6,809,346 B2 | 10/2004 | Udagawa |
| 6,960,626 B2 | 11/2005 | Takekoshi et al. |
| 6,962,968 B2 | 11/2005 | Phelps et al. |
| 6,994,914 B2 | 2/2006 | Winckler et al. |
| 7,022,806 B2 | 4/2006 | Faler |
| 2004/0155380 A1 | 8/2004 | Kendall et al. |
| 2004/0188883 A1 | 9/2004 | Barron et al. |
| 2005/0059768 A1 | 3/2005 | Dion et al. |
| 2005/0288176 A1 | 12/2005 | Kuhlman |
| 2005/0288420 A1 | 12/2005 | Paquette |
| 2006/0003887 A1 | 1/2006 | Paquette |
| 2006/0004135 A1 | 1/2006 | Paquette |

FOREIGN PATENT DOCUMENTS

| | | |
|---|---|---|
| EP | 543492 A1 | 5/1993 |

| | | | |
|---|---|---|---|
| EP | 0566313 A2 | 10/1993 |
| EP | 589640 A1 | 3/1994 |
| EP | 598604 A1 | 5/1994 |
| EP | 601753 A1 | 6/1994 |
| EP | 635512 A1 | 1/1995 |
| EP | 655476 A1 | 5/1995 |
| EP | 436186 B1 | 10/1995 |
| EP | 688778 A1 | 12/1995 |
| EP | 714926 A2 | 6/1996 |
| EP | 699701 A3 | 9/1996 |
| EP | 0798336 A2 | 1/1997 |
| EP | 1111012 A9 | 6/2001 |
| EP | 0 594 385 | 5/2003 |
| EP | 1 308 208 A1 | 7/2003 |
| EP | 1 354 908 | 10/2003 |
| EP | 1 378 540 | 1/2004 |
| EP | 1 420 036 A2 | 5/2004 |
| EP | 1 475 402 A1 | 11/2004 |
| EP | 1 409 475 B1 | 10/2005 |
| FR | 2 530 628 | 1/1984 |
| GB | 798412 | 8/1954 |
| GB | 957841 | 5/1964 |
| GB | 991020 | 5/1965 |
| GB | 1044205 | 9/1966 |
| GB | 1108921 | 4/1968 |
| GB | 1273225 | 5/1972 |
| GB | 1349324 | 4/1974 |
| GB | 2 123 405 A | 2/1984 |
| JP | 4621873 | 6/1971 |
| JP | 476425 | 10/1972 |
| JP | 57-122078 A | 7/1982 |
| JP | 6275547 | 4/1987 |
| JP | 62141063 A | 6/1987 |
| JP | 63156824 A | 11/1988 |
| JP | 02298512 | 12/1990 |
| JP | 4253764 | 9/1992 |
| JP | 08-093594 | 4/1996 |
| JP | 09048876 | 2/1997 |
| JP | 09-110832 | 4/1997 |
| JP | 09-238806 | 9/1997 |
| JP | 10-069915 | 3/1998 |
| JP | 10-194262 | 7/1998 |
| JP | 11-136942 | 5/1999 |
| JP | 2001031846 | 2/2001 |
| JP | 2002293902 | 10/2002 |
| JP | 2002293903 | 10/2002 |
| JP | 2002308969 | 10/2002 |
| JP | 2002317041 | 10/2002 |
| JP | 02320499 | 11/2002 |
| JP | 02322272 | 11/2002 |
| JP | 02338672 | 11/2002 |
| JP | 2003082081 | 3/2003 |
| SU | 1077893 | 3/1984 |
| SU | 1532560 A1 | 12/1989 |
| WO | 88/ 06605 | 9/1988 |
| WO | 91/09899 | 7/1991 |
| WO | 93/ 04106 | 3/1993 |
| WO | 95/00574 | 1/1995 |
| WO | 95/30702 | 11/1995 |
| WO | 96/22319 | 7/1996 |
| WO | 99/25485 | 5/1999 |
| WO | 00/27632 | 5/2000 |
| WO | 00/38897 | 7/2000 |
| WO | 01/53379 A1 | 7/2001 |
| WO | 01/56694 A1 | 8/2001 |
| WO | 02/18476 A2 | 3/2002 |
| WO | 02/22738 A2 | 3/2002 |
| WO | 02/098946 A1 | 12/2002 |
| WO | 02/098947 A1 | 12/2002 |
| WO | 03/002551 A1 | 1/2003 |
| WO | 2003/002551 | 1/2003 |
| WO | 03/031496 A1 | 4/2003 |
| WO | 2003/031059 | 4/2003 |
| WO | 03/080705 A1 | 10/2003 |
| WO | 2003/080705 | 10/2003 |
| WO | 2004/058471 | 7/2004 |
| WO | 2004/058854 | 7/2004 |
| WO | 2004/058868 | 7/2004 |
| WO | 2004/058872 | 7/2004 |
| WO | 2004/060640 | 7/2004 |
| WO | 2005/090508 | 9/2005 |
| WO | 2005/105889 | 11/2005 |

OTHER PUBLICATIONS

Beach, A. Christopher G. "The Preparation of Mirrors by Sputtering Metals onto Glass Surfaces," *A. Inst. P.*, Chelsea Polytechnic, M.S. received, Mar. 17, 1930.

Brunelle (1995) "Macrocyles For The Synthesis of High Molecular Weight Polymers" pp. 197-235, ch. 6, New Methods of Polymer Synthesis: vol. 2, edited by J.R. Ebdon and G.C. Eastmond.

Brunelle et al. (1997) "Semi-crystalline Polymers via Ring-Opening Polymerization: Preparation and Polymerization of Alkylene Phthalate Cyclic Oligomers" *Polymers Preprints* vol. 38, No. 2, pp. 381-382.

Brunelle et al. (1998) "Semicrystalline Polymers via Ring-Opening Polymerization: Preparation and Polymerization of Alkylene Phthalate Cyclic Oligomers" *Macromolecules* vol. 31, No. 15, pp. 4782-4790.

Burch, R. R. et al. (2000) "Synthesis of Cyclic Oligoesters and Their Rapid Polymerization to High Molecular Weight" Macromolecules, vol. 33, No. 14, 5053-5064.

Chisholm et al. "Syntheses and structural characterization of 2,2'-methylene-bis(6-*t*-butyl-4-methyl-phenoxide) complexes of titanium, zirconium and tantalum," *Polyhedron*, vol. 16, No. 17, (1997) pp. 2941-2949.

Cotton, N. J. et al. (1993) "Rate and Extent of Supercritical Fluid Extraction of Cyclic Trimer from Poly(Ethylene Terephthalate) at Elevated Temperatures" *Journal of Chromatographic Science*, vol. 31, No. 5, 157-161.

Cussler et al. "Barrier Membranes," *Journal of Membrane Science*, 38 (1988) pp. 161-174.

Deleuze et al. (1998) "Polymer-Supported Titanates as Catalysts for Transesterification Reactions" *Polymer*, vol. 39, No. 24, pp. 6109-6114.

Deleuze et al. (2000) "Synthesis of Porous Supports Containing N-(*p*-hydroxyphenyl)- or N-(3-4-dihydroxybenzyl) Maleimide-Anchored Titanates and Application as Catalysts for Transesterification and Epoxidation Reactions" *Journal of Polymer Science*, vol. 38, pp. 2879-2886.

DuPont™ Zonyl® Fluorosurfactants Dupont The Miracles of Science "Chemicals to Enhance Your Product's Performance" http://www.dupont.com/zonyl/perform.html, last searched on May 16, 2002 and pp. 1-3 downloaded on May 16, 2002.

Durfee et al. "Chemical and Electrochemical Reduction of Titanium (IV) Aryloxides," *Inorganic Chemistry*, 24 (1985) pp. 4569-4573.

Fantacci et al. "Density Functional Study of Tetraphenolate and Calix[4]arene Complexes of Early Transition Metals," *Inorganic Chemistry*, 40 (2001) pp. 1544-1549.

Fukushima et al. "Graphite Nanoplatelets as Reinforcements for Polymers: Structural, Electrical and Thermal Properties," *Proc. 2nd Ann., Automotive Comp. Conf., Soc. Plast. Eng.*, Sep. 2002, 7 pgs.

Fukushima et al. "Synthesis of an Intercalated Compound of Montmorillonite and 6-Polyamide," *Journal of Inclusion Phenomena*, 5 (1987) pp. 473-482.

Hall et al. "Recent research on the synthesis and applications of cyclic oligomers," *Reactive & Functional Polymers*, 41 (1999), pp. 133-139.

Hamb et al. Synthesis of Cyclic Tris(Ethylene Terephthalate), *Polymer Letters*, 5 (1967), pp. 1057-1058.

Hamilton et al. (1998) "Cyclic Polyesters: Part 8. Preparation and Characterization of Cyclic Oligomers in Six Aromatic Ester and Ester—Ester Systems", *Polymer* vol. 39, No. 14., 3241-3252.

Harrison, A. G. et al. (1997) "Analysis of cyclic oligomers of poly(ethylene terephthalate) by liquid chromatography/mass spectrometry" Polymer Communications, vol. 38, No. 10, 2549-2555.

Henshaw et al. (1994) "Recycling of a Cyclic Thermoplastic Composite Material by Injection and Compression Molding" *J. of Thermoplastic Composite Materials* vol. 7 (1), 14-29.

Hubbard, P. A. (1996) "Polyesters via Macrocyclic Oligomers" Dissertation presented at the University of Akron.

Kricheldorf, H. R. et al. (1997) "Macrocycles IV. Macrocyclic Polylactones as Bifunctional Monomers for Polycondensations" *Journal of Polymer Science*, vol. 36, No. 9, 1373-1378.

Kricheldorf, H. R. et al. (1998) "Macrocycles. 3. Telechelic Polylactones via Macrocyclic Polymerization" Macromolecules, vol. 31, No. 3, 614-620.

Lancaster Results, Titanium (IV), http://www.lancastersynthesis.com/home_quick_search.htm; pp. 1-3 downloaded on Nov. 29, 2001; last searched on Apr. 22, 2002 and pp. 4-8 downloaded on Apr. 22, 2002.

Lattimer et al. (1998) "MALDI-MS Analysis of Pyrolysis Products From a Segmented Polyurethane" *Journal of Analytical and Applied Pyrolysis*, vol. 48, 1-15.

Lewis et al. (1999) "A Highly Efficient Preparation of Methacrylate Esters using Novel Solid Phase Titanium-Based Transesterification Catalysts" *Synlett*, pp. 957-959.

Liu et al. (1999) "Preparation of Cyclic Polyester Oligomers and Ultra-low VOC Polyester Coatings" *Polymer Preprints*, vol. 40, No. 1.

Martin et al. (1987) "Pultrusion", *Engineered Materials Handbook*: vol. 1 *Composites*, pp. 533-543.

Miller, S. (1998) "Macrocyclic polymers from cyclic oligomers of poly(butylene terephthalate)" Dissertation Presented at University of Massachusetts, Amherst, MA US.

Mueller, F. J. et al. (1983) "Synthesis of Cyclic Oligomers of Butylene Terephthalate" *Makromol. Chem.*, vol. 184, No. 12, 2487-95.

Mueller, F. J. et al. (1983) "Synthesis of Cyclic Oligomers of Butylene Terephthalate" *Makromol. Chem.*, vol. 184, No. 12, 2487-95. (Translation).

Okuda et al. "Synthesis and Characterization of Mononuclear Titanium Complexes Containing a Bis(phenoxy) Ligand Derived from 2,2'-Methylene-bis(6-*tert*-butyl-4-methylphenol)," *Chem. Ber.*, vol. 128, (1995) pp. 221-227.

Perovic, A. (1985) "Morphological Instability of poly(ethylene terephthalate) cyclic oligomer crystals" *Journal of Material Science*, vol. 20, Iss. 4, 1370-1374.

Perovie et al. (1982) "Crystallization of Cyclic Oligomers in Commerical Poly(ethleneterephthalate) Films" *Polymer Bulletin* vol. 6, 277-283.

Product Detail and structure Image, Titanium (IV) butoxide, polymer, http://www.sigmaaldrich.com/cgi-in/hsrun/Distributed/HahtShop/HahtShop.htx;start=HS_FramesetMain; last searched on Mar. 27, 2002 and pp. 1-2 downloaded on Mar. 27, 2002.

Roelens, S. (1988) "Organotin-Mediated Synthesis of Macrocyclic Polyesters: Mechanism and Selectivity in the Reaction of Dioxastannolanes with Diacyl Dichlorides" *Journal of the Chemical Society, Perkin Transactions 2*, vol. 8, 1617-1625.

Ruddick et al. "A new method for the polymer-suported synthesis of cyclic oligoesters for potential applications in macrocyclic lactone synthesis and combinatorial chemistry," *J. Chem. Soc., Perkin Trans. 1*, 2002, pp. 627-637.

Spanagel et al. "Macrocyclic Esters," Contribution No. 153 from The Experimental Station of E.I. duPont deNemours & Company, vol. 57, pp. 929-934 (May 1935).

Toth et al. "Towards supported catalyst models: the synthesis, characterization, redox chemistry, structures of the complexes Ti(Oar')$_4$ (Ar'=C$_6$H$_4$(2-*t*-Bu), C$_6$H(2,3,5,6-Me)$_4$)," *Canadian Journal of Chemistry*, vol. 69, (1991) pp. 172-178.

Uhi et al. "Flame Retarduncy of Graphite Nanocomposites," *Polym. Mater. Sci. Eng.* 83:56(2000).

Usuki et al. "Swelling behavior of montmorillonite cation exchanged for ω-amino acids by-ϵ-caprolactam," *J. Mater. Res.*, vol. 8, No. 5, May 1993, pp. 1174-1178.

Usuki et al. "Synthesis of nylon 6-clay hybrid," J. Mater. Res., vol. 8, No. 5, May 1993, pp. 1179-1184.

Ward et al. "Gas barrier improvement using vermiculite and mica in polymer films," *Journal of Membrane Science*, 55 (1991) pp. 173-180.

Xiao et al. "Preparation of exfoliated graphite/polystyrene composite by polymerization-filling technique," *Polymer*, 42 (2001) pp. 4813-4816.

Youk et al. "Polymerization of Ethylene Terephthalate Cyclic Oligomers with Antimony Trioxide," *Macromolecules*, 33 (2000), pp. 3594-3599.

U.S. Appl. 10/102,162, filed Mar. 20, 2002, Wang et al.

Communication pursuant to Article 96(2) EPC for 01942649.3-2102, Jan. 9, 2004.

Communication pursuant to Article 96(2) EPC for 01968413.3-2102, Dec. 3, 2004.

Communication pursuant to Article 96(2) EPC for 01968581.7-2102, Nov. 11, 2003.

Communication pursuant to Article 96(2) EPC for 02734665.9-2102, Dec. 3, 2005.

Communication pursuant to Article 51(4) EPC for 02756358.4-2117, Apr. 2, 2005.

Communication pursuant to Article 96(2) EPC for 02756358.4-2117, May 6, 2004.

Bagshaw et al., "Templating of Mesoporous Molecular Sieves by Nonionic Polyethylene Oxide Surfactants," Science, 269, p. 1242, Sep. 1, 1995.

Kaviratna et al., "Synthesis Polyether-Clay Nanocomposites: Kinetics of Epoxide Self-Polymerization in Acidic Smectite Clays," Polym. Prep., 31(1), 788 (1994).

Kojima et al., "Mechanical properties of nylon 6-clay hybrid," J. Mater. Res., 8, (1993).

Lee, J. et al., "Fire Retardent Polyetherimide Nanocomposites," Matter Res. Soc. Proc. 457, 513-518, (1997).

Lee, S.-S. et al., "Synthesis of PET-Layered Silicate Nanocomposites Using Cyclic Ester Oligomers," Polymeric Materials: Science and Engineering, 89, 370-1 (2003).

Messersmith et al., "Polymer-Layered Silicate Nanocomposites: In Situ Intercalative Polymerization of ϵ-Caprolactone in Layered Silicates," Chem. Mater., 5, 1064 (1993).

Nazar, et al., "Synthesis and Properties of a New (PEO)x[Na(H2O)]0.25MoO3 Nanocomposites," J. Mater. Res., 5(11), 1985 (1995).

Okada, et al., "Synthesis and Characterization of a Nylon 6-Clay Hybrid," Polym. Prep., 28, 447, (1987).

Oriakhi et al., "Poly(Pyrrole) and Poly(Thiophene) / Clay Nanocomposites Via Latex-Colloid Interaction," Mater. Res. Bull., 30, No. 6, p. 723, (1995).

Scatteia et al., "Rheology of PBT-Layered Silicate Nanocomposites Prepared by Melt Compounding," Plastics, Rubbers and Composites, 33, 85-91 (2004) and references therein.

Tripathy, et al., "Poly(Butylene Terephthalate) Nanocomposites Prepared by In-Situ Polymerization," Macromolecules, 36, 8593-5 (2003).

Vankelecom et al. "Incorporation of Zeolites in polyimide Membranes," J. Phys. Chem., 99, 13187 (1995).

Yano, K. et al., "Synthesis and Properties of Polyimide-Clay Hybrid," J. Polym. Sci., Part A, Polym. Chem., 31, 2493 (1993).

EPO Online Patent Register and Public File Inspection, European patent application No. EP20030714278.

Pre-examination Amendment filed Oct. 8, 2004, European patent application No. EP20030714278.

First Examination Report (with Annex) issued Nov. 25, 2004, European patent application No. EP20030714278.

Reply to First Examination Report filed Mar. 24, 2005, European patent application No. EP20030714278.

Second Examination Report (with Annex) issued Apr. 6, 2005, European patent application No. EP20030714278.

Reply to Second Examination Report filed Jul. 27, 2005, European patent application No. EP20030714278.

Futher Reply to Second Examination Report filed Aug. 10, 2005, European patent application No. EP20030714278.

Third Examination Report (with Annex) issued Aug. 18, 2005, European patent application No. EP20030714278.

Reply to Third Examination Report filed Dec. 9, 2005, European patent application No. EP20030714278.

* cited by examiner

CATALYTIC SYSTEMS

This application is a divisional of U.S. patent application Ser. No. 10/102,162, filed Mar. 20, 2002 now U.S. Pat. No. 6,906,147, the entirety of which is incorporated herein by reference.

TECHNICAL FIELD

This invention generally relates to catalytic systems. More particularly, the invention relates to aryl titanate compounds useful as catalysts and co-catalysts in single-component and multi-component catalytic systems for the polymerization of macrocyclic oligoesters and the depolymerization of polyesters.

BACKGROUND INFORMATION

Linear polyesters such as poly(alkylene terephthalate) are generally known and commercially available where the alkylene typically has 2 to 8 carbon atoms. Linear polyesters have many valuable characteristics including strength, toughness, high gloss, and solvent resistance. Furthermore, polyesters may be fabricated into articles of manufacture by a number of well-known techniques including injection molding, roto-molding, and extrusion.

Recently, macrocyclic oligoesters were developed as precursors to polyesters. Macrocyclic oligoesters exhibit low melt viscosity, which can be advantageous in certain applications. Furthermore, certain macrocyclic oligoesters melt and polymerize at temperatures well below the melting point of the resulting polymer. Upon melting and in the presence of an appropriate catalyst, polymerization and crystallization can occur virtually isothermally.

Single-component catalysts that have been developed for use in the polymerization of macrocyclic oligoesters include various organo-metal compounds, including conventional titanate esters. The required volume ratio of a macrocyclic oligoester to a conventional titanate ester is very high, typically greater than 100:1. See, e.g., U.S. Pat. No. 5,466,744 to Evans et al. The high volume ratio requires sophisticated and costly metering and mixing equipment to properly introduce and disperse the relatively small amount of catalyst. This is of particular concern in liquid molding and extrusion applications.

Furthermore, it is desirable to develop catalytic systems of increased versatility to better control the onset and speed of polymerization without the need for costly metering and mixing equipment. For instance, it is desirable to develop catalytic systems which do not appreciably begin to catalyze a reaction until an appropriate time, and which allow the reaction to take place quickly and relatively homogeneously throughout the reaction mixture once reaction is initiated.

SUMMARY OF THE INVENTION

Single-component and multi-component catalytic systems using titanium-containing compounds (e.g., aryl titanates) have been developed which solve the above-identified problems. For example, such catalytic systems are particularly useful for the polymerization of macrocyclic oligoesters in liquid molding applications such as structural reaction injection molding and resin transfer molding. These catalytic systems are also useful in the depolymerization of polyester.

Multi-component catalytic systems that have been developed include systems using aryl titanates in combination with alcohols. These catalytic systems allow for increased versatility in certain applications such as liquid molding. For example, two-component catalytic systems have been developed for the polymerization of macrocyclic oligoesters where each component can be mixed with separate fractions of molten macrocyclic oligoester, thereby permitting two separate streams of macrocyclic oligoester to be mixed together to initiate catalysis. Each separate stream is relatively inactive over a period of time, allowing sufficient time for mixing of the co-catalysts with the macrocyclic oligoester. Upon contact of the two streams, for example, inside a mold or a pre-mold mixer, the polymerization reaction is initiated quickly, and the polymerization of macrocyclic oligoester may be complete within minutes. Because the volume ratio of each of the two streams may be maintained in the range of about 1:1 to 20:1, there is a reduced need for sophisticated metering and mixing equipment. Also, since certain macrocyclic oligoesters melt and polymerize at temperatures well below the melting point of the resulting polymer, polymerization and crystallization can occur virtually isothermally. Thus, a polymerized product may be removed from a mold without cooling it following polymerization.

In one aspect, the invention is directed to a catalytic system that includes a first component and a second component. The first component typically includes a Ti-containing compound, and the second component includes an alcohol. The catalytic activity of the system increases upon contact of the first component and the second component.

In another aspect, the invention is directed to a method for polymerizing a macrocyclic oligoester having a structural repeat unit of the formula

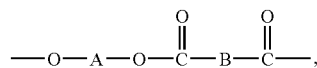

where A is an alkylene, a cycloalkylene, or a mono- or polyoxyalkylene group; and B is a divalent aromatic or alicyclic group. The method generally includes the steps of providing a first compound, providing a second compound, and contacting the first compound, the second compound, and a macrocyclic oligoester to polymerize the macrocyclic oligoester. The first compound and the second compound define at least part of a catalytic system, wherein the catalytic activity of the system increases upon contact of the first compound and the second compound.

In yet another aspect, the invention is directed to a method for making a co-polyester. The method generally includes the steps of providing a metal-containing compound, providing a diol having a molecular formula

and contacting the metal-containing compound and the diol in the presence of a macrocyclic oligoester, thereby producing a polyester having a structural unit of R, where R is an organic group In yet another aspect, the invention is directed to a method for depolymerizing a polyester. The method generally includes the steps of providing a polyester, providing a depolymerization catalyst that includes a compound with the molecular formula

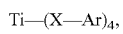

and contacting the polyester with the depolymerization catalyst. Each X independently is O, S, or N. Each Ar group may independently be an organic group which includes an aromatic group. Alternatively, two or more Ar groups taken together may form an organic group which includes an aromatic group.

In yet another aspect, the invention is directed to a method for polymerizing a macrocyclic oligoester. The method generally includes the steps of providing a macrocyclic oligoester, providing a polymerization catalyst having a compound with the molecular formula Ti—(X—Ar)$_4$, and contacting the macrocyclic oligoester with the polymerization catalyst, thereby polymerizing the macrocyclic oligoester. Each X independently is O, S, or N. Each Ar group may independently be an organic group which includes an aromatic group. Alternatively, two or more Ar groups taken together may form an organic group which includes an aromatic group.

In yet another aspect, the invention is directed to a catalyst that includes a Ti-containing compound having the molecular formula Ti—(X—Ar)$_4$.

Each X independently is O, S, or N. Each Ar group may independently be an organic group which includes an aromatic group that is directly bonded to at least one X. Alternatively, two or more Ar groups taken together may form an organic group which includes an aromatic group that is directly bonded to at least one X. Each aromatic group independently is substituted with a bulky group at at least one ortho-position and/or is directly bonded to at least two X's.

In yet another aspect, the invention is directed to a composition including a macrocyclic oligoester and a compound having the molecular formula Ti—(X—Ar)$_4$.

Each X independently is O, S, or N. Each Ar group may independently be an organic group which includes an aromatic group. Alternatively, two or more Ar groups taken together may form an organic group which includes an aromatic group.

In yet another aspect, the invention is directed to a catalyst that includes a compound having the molecular formula (R—Y$^1$—)$_i$-M-(—Y$^2$—Ar)$_j$.

Each of i and j are integers such that $i \geq 0$ and $j \geq 1$. The sum of i and j is either 4 or 6. Each Y$^1$ may independently be a single bond. Alternatively, each Y$^1$ may be either a —O— (CH$_2$)$_x$— group where x is 1, 2, or 3, or a heteroatom selected from the group consisting of O, S, and N. Each Y$^2$ independently is O, S, or N. Each R group may independently be a substituted or unsubstituted alkyl group or a substituted or unsubstituted alkyl ether group. Alternatively, two or more R groups taken together may be a substituted or unsubstituted alkyl group or a substituted or unsubstituted alkyl ether group. Each Ar group may independently be an organic group which includes an aromatic group that is directly bonded to at least one Y$^2$. Alternatively, two or more Ar groups taken together may form an organic group which includes an aromatic group that is directly bonded to at least one Y$^2$. Each aromatic group independently is substituted with a bulky group at at least one ortho-position. M is either Ti or Sn.

DESCRIPTION

According to the present invention, single-component and multi-component catalytic systems using titanium-containing compounds, such as aryl titanates, are prepared that are useful in various applications, such as the polymerization of macrocyclic oligoesters. Also according to the present invention, multi-component catalytic systems are prepared, including systems using aryl titanates in combination with alcohols, that are useful in various applications, such as the polymerization of macrocyclic oligoesters in liquid molding applications. These new catalytic systems offer various advantages such as the improved ability to control the timing of the initiation of reaction, as well as the speed of the reaction. Another advantage is the improved ease of handling the introduction and mixing of reactant and catalysts. As used here, the term "reactant" may include one or more compounds. Both advantages may be realized without the need for costly mixing and/or metering equipment to maintain homogeneity of the mixture.

Definitions

The following general definitions may be helpful in understanding the various terms and expressions used in this specification.

As used herein, a "macrocyclic" molecule means a cyclic molecule having at least one ring within its molecular structure that contains eight or more atoms covalently connected to form the ring.

As used herein, an "oligomer" means a molecule that contains two or more identifiable structural repeat units of the same or different formula.

As used herein, an "oligoester" means a molecule that contains two or more identifiable ester functional repeat units of the same or different formula.

As used herein, a "macrocyclic oligoester" means a macrocyclic oligomer containing two or more identifiable ester functional repeat units of the same or different formula. A macrocyclic oligoester typically refers to multiple molecules of one specific formula having varying ring sizes. However, a macrocyclic oligoester may also include multiple molecules of different formulae having varying numbers of the same or different structural repeat units. A macrocyclic oligoester may be a co-oligoester or multi-oligoester, i.e., an oligoester having two or more different structural repeat units having an ester functionality within one cyclic molecule.

As used herein, a "filler" means a material other than a macrocyclic oligoester or a polymerization catalyst that may be included in a catalytic system. A filler may be included to achieve a desired purpose or property, and may be present in a resulting polyester product, for instance. Purposes include providing chemical, thermal, or light stability, providing weight or bulk, providing flame resistance, substituting a more expensive material, facilitating processing, and/or providing other desirable properties as recognized by a skilled artisan. Illustrative examples of fillers are, among others, fumed silica, titanium dioxide, calcium carbonate, chopped fibers, fly ash, glass microspheres, micro-balloons, crushed stone, nanoclay, linear polymers and monomers, and combinations thereof.

As used herein, an "alkylene group" means substituted or unsubstituted —C$_n$H$_{2n}$—, where $2 \leq n \leq 15$.

As used herein, an "alkyl ether group" means two alkyl groups linked together by an oxygen atom.

As used herein, an "alicyclic group" means a non-aromatic hydrocarbon group containing a cyclic structure.

As used herein, a "cycloalkylene group" means a cyclic alkylene group, —$C_nH_{2n-x}$—, where x represents the number of H's replaced by cyclization(s).

As used herein, a "mono- or polyoxyalkylene group" means [—$(CH_2)_m$—O—]$_n$—$(CH_2)_m$—, wherein n is an integer greater than zero and m is an integer greater than one.

As used herein, a "divalent aromatic group" means an aromatic group with two links to other parts of the macrocyclic molecule. For example, a divalent aromatic group may include a meta- or para-linked monocyclic aromatic group (e.g., benzene).

As used herein, an "acyclic group" is a group that does not contain a cyclic molecular structure.

As used herein, an "organic group" is a group that contains at least one carbon atom. Exemplary organic groups include alkyl groups, alkoxy groups, and aryl groups. An organic group may be mono- or di-valent. An organic group may include one or more inorganic moieties. An organic group may be substituted or unsubstituted, branched or unbranched, saturated or unsaturated, and cyclic or acyclic.

As used herein, a "bulky group" is a group that is larger than —$CH_3$. Exemplary bulky groups include ethyl groups, propyl groups, butyl groups, trichloromethyl, and —$CH_2OH$, among others.

As used herein an atom at a "1-position" refers to an atom in an aryl group which is directly bonded to an atom X in the formula M-(X—Y)$_i$, where i is an integer greater than zero, M is a metal which may be additionally substituted, X is O, S, or N, and Y is an aryl group.

As used herein, an atom at an "ortho-position" refers to an atom that (a) is not at a 1-position, and (b) is directly bonded to an atom at a 1-position. Substitution at an ortho-position is replacement of an atom (e.g., H atom) in an Ar group which is directly bonded to an atom in an ortho-position. The use of the term "ortho" here does not imply that the atom at either the 1-position or the ortho-position is a carbon atom, nor does it imply that the ring structure of the Ar group is made up of any particular number of atoms. For example, titanium (IV) 2-tert-butyl-6-methyl phenoxide has the following structure:

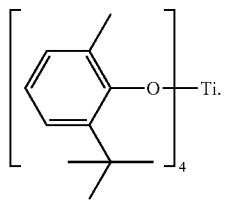

This compound has an aromatic group that is substituted at one ortho-position (the 2-position) with a tert-butyl group and at another ortho-position (the 6-position) with a methyl group. Another example of a compound that is substituted at an ortho-position is titanium (IV) 2,4-dicumyl phenoxide, which has the following structure:

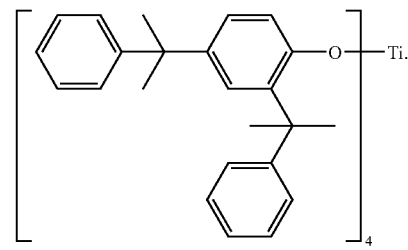

This compound has an aromatic group that is substituted at one ortho-position (the 2-position) with a cumyl group.

As used herein, a "polyol" is an alcohol having 2 or more hydroxyl groups.

As used herein, a "polyepoxide" is an epoxide having 2 or more oxirane (e.g., ethylene oxide) groups.

As used herein, an "accelerator" is a substance which increases the rate of a reaction, usually by acting in conjunction with a catalyst.

I. Multi-Component Catalytic Systems

A catalytic system includes one or more components which may or may not be catalysts themselves, and may optionally include other compounds, such as various additives. Generally, a catalyst is a substance that increases the rate of a chemical reaction without itself being substantially consumed or if being substantially consumed, the consumption is ancillary to the reaction itself. Illustrative examples of catalysts include metals, alloys, intermetallic compounds, oxides, salts, sulfides, acids, bases, bifunctional compounds, organic ion exchangers, metal coordination complexes (e.g., Ziegler-Natta catalysts), zeolites, and enzymes. Catalysts may be supported, unsupported, precipitated, impregnated, skeletal, fused, molten, dried, calcinated, and reduced, for instance. Illustrative examples of chemical reactions that may be catalyzed by one or more catalysts include polymerization reactions, depolymerization reactions, transesterification reactions, radical chain reactions, and nucleophilic substitution reactions.

Conventional single-component catalytic systems contain only one catalyst. These one-component catalytic systems may not provide the versatility needed for some applications. For example, conventional organo-metal catalysts that may be suitable for use in the polymerization of macrocyclic oligoesters include various titanate esters, such as tetraisopropyl titanate, and various organotin compounds, such as di-n-butyltin (IV) oxide. Using such catalysts, however, typically requires the dispersal of a relatively small volume of catalyst into a relatively large volume of reactant (the reactant may comprise one or more compounds). For example, the volume ratio of reactant to catalyst is typically greater than 100:1. In addition, the above catalysts typically cause the desired reaction to begin as soon as the reactant and the catalyst are mixed. The timing of this mixing, and hence the start of catalyzation, as well as the thoroughness of mixing, are important to control before or during certain applications, such as liquid molding (e.g, injection molding and resin transfer molding), compression molding, vacuum bagging and resin film infusion, slurry processing, extrusion, pultrusion, rotational molding, belt pressing, and single or twin-screw compounding. The mixing may occur inside or outside of a mold. It can be difficult to control the timing and thoroughness of such mixing in one-component catalytic systems.

Multi-component catalytic systems have been developed which provide increased versatility, allowing improved ability to precisely control the onset of reaction and to provide introduction mechanisms that do not involve large volume ratios of reactants to catalyst before or during mixing in a mold, for instance. Separate components of such a catalytic system may be divided among two or more streams of reactant(s) of comparable volume. Reaction of the reactant(s) is effectively delayed until each of the components of the catalytic system are brought into contact. Because the components of the catalytic system are separated among two or more streams, reaction does not appreciably occur until the two or more streams are brought into contact with each other. The individual components may be introduced to individual streams of reactant in advance of the contact of all the streams, so that there is sufficient time or sufficient intermediary processing steps for the sufficient mixing of the relatively small amounts of components of the catalytic system with the relatively large amounts of reactant. Since the streams of reactant may be maintained at comparable volumes, there is no need for special mixing or metering equipment as would be required for single-component catalytic systems, which require dispersal of a relatively small quantity of a single catalyst into a relatively large volume of reactant mixture. Upon contact of the streams, the reaction may occur quickly and homogeneously.

For example, two-component catalytic systems have been developed for the polymerization of macrocyclic oligoesters wherein each component can be mixed with molten macrocyclic oligoester, thereby permitting two separate reactant streams. Each separate stream is relatively inactive over a period of time, ranging from minutes to hours, allowing sufficient time for mixing of the individual components of the catalytic system with the macrocyclic oligoester. Upon contact of the two streams, for example, inside a mold or a pre-mold mixer, the polymerization reaction begins almost immediately, and the polymerization of macrocyclic oligoester may be complete within minutes. Because the volume ratio of each of the two streams may be maintained in the range of about 1:1 to 3:1, there is no need for sophisticated metering and mixing equipment.

In one aspect, the invention is directed to a catalytic system that includes a first component and a second component. The first component includes a Ti-containing compound, and the second component includes an alcohol, an epoxide, or both. The catalytic activity of the system in the presence of one or more reactants increases upon contact of the first component and the second component.

In one embodiment, the Ti-containing compound in the first component has the molecular formula $$(R-Y^1-)_i-Ti-(-Y^2-Ar)_j.$$

Each of i and j are integers such that $i \geq 0$ and $j \geq 1$. The sum of i and j is either 4 or 6. Each $Y^1$ may independently be a single bond. Alternatively, each $Y^1$ may be a $-O-(CH_2)_x-$ group where x is 1, 2, or 3, or a heteroatom selected from the group consisting of O, S, and N. Each $Y^2$ independently is O, S, or N.

Each R group independently is an alkyl group or an alkyl ether group. The alkyl group and the alkyl ether group may be branched or unbranched, cyclic or acyclic, and substituted or unsubstituted. R may contain substitution groups including halogen, hydroxyl, alkoxy, and carbonyl groups, for example. Additionally, two or more R groups may be attached to form either an alkyl group or an alkyl ether group, which may be branched or unbranched, cyclic or acyclic, and substituted or unsubstituted. Illustrative examples of alkyl groups include methyl, ethyl, propyl, isopropyl, n-butyl, isobutyl, and pentyl groups. Illustrative examples of alkyl ether groups include diethyl ether, methyl-ethyl ether, methyl-n-propyl ether, methyl-isopropyl ether, and di-n-butyl ether groups.

Each Ar group may independently be an organic group which includes an aromatic group that is directly bonded to at least one $Y^2$. Alternatively, two or more Ar groups taken together may form an organic group which includes an aromatic group that is directly bonded to at least one $Y^2$. The organic group and/or the aromatic group may be substituted or unsubstituted. The aromatic group may include a 5-membered ring, a 6-membered ring, and/or a 7- or higher-membered ring. The members of the ring may include carbon, or one or more heteroatoms such as S, N, or O, for instance. The aromatic group may include one or more rings connected together in any configuration.

Illustrative examples of ring structures of the aromatic group include structures that are combinations of one or more 6-membered rings, such as structures comprising benzene, naphthalene, anthracene, phenanthrene, and chrysene. Other illustrative examples of ring structures of the aromatic group include aromatic heterocyclic structures, such as the structures comprising pyridine, furan, thiophene, pyrrole, and oxazole. Still other illustrative examples of ring structures of the aromatic group include monocyclics and polycyclics with a 5-membered ring, such as the structures comprising cyclopentadiene, indene, fluorene, indole, and purine.

In certain embodiments, i=0, j=4, and $Y^2$ is O, such that the Ti-containing compound has the molecular formula $$Ti-(-O-Ar)_4.$$

In certain of these embodiments, each aromatic group independently is substituted at at least one ortho-position. Additionally, each aromatic group may be directly bonded to at least two O's, or each aromatic group may be both substituted at at least one ortho-position and directly bonded to at least two O's. Illustrative examples of substitution groups include alkyl groups and alkyl ether groups, which may be branched or unbranched, cyclic or acyclic, and substituted or unsubstituted. Illustrative examples of alkyl groups include methyl, ethyl, propyl, isopropyl, n-butyl, isobutyl, and pentyl groups. Illustrative examples of alkyl ether groups include diethyl ether, methyl-ethyl ether, methyl-n-propyl ether, methyl-isopropyl ether, and di-n-butyl ether groups. Other illustrative substitution groups include halogen, hydroxyl, carbonyl, and alkoxy groups.

Without wishing to be bound to any particular theory, it is believed that ortho-substitutions of each aromatic group and/or direct bonding of each aromatic group to at least two O's sterically and/or electronically hinder chemical attack of the Ti—O bond, thereby inhibiting the catalytic activity of the Ti-containing compound. The Ti-containing compound is relatively inactive compared to its unhindered counterparts. An example of how this relative inactivity may be useful is that it may allow sufficient time for mixing of the Ti-containing compound with reactant before being brought into contact with a second component including an alcohol or an epoxide, whereupon the catalytic activity of the catalytic system is increased.

In certain embodiments, each aromatic group independently is substituted with a bulky group at at least one ortho-position. Illustrative examples of bulky groups include alkyl groups with two or more carbon atoms and alkyl ether groups, which may be branched or unbranched, cyclic or acyclic, and substituted or unsubstituted. Illustrative examples of bulky alkyl groups include ethyl, propyl, iso-propyl, n-butyl, isobutyl, and pentyl groups. Illustrative examples of bulky alkyl ether groups include diethyl ether, methyl-ethyl ether, methyl-n-propyl ether, methyl-isopropyl ether, and di-n-butyl ether groups. The bulky groups themselves may include halogen, hydroxyl, alkoxy, and carbonyl substitution groups.

Without wishing to be bound by any particular theory, it is believed that ortho-substitution of each aromatic group with a bulky group sterically may hinder chemical attack of the Ti—O bond, thereby inhibiting the catalytic activity of the Ti-containing compound. The Ti-containing compound is relatively inactive compared to its unhindered counterparts. The relative inactivity of the catalyst may allow sufficient time for mixing of the Ti-containing compound with reactant before being brought into contact with the second component of the catalytic system, whereupon catalytic activity is increased.

In certain embodiments, the Ti-containing compound is one of the compounds in Table 1.

TABLE 1

Ti-containing Compounds

Titanium (IV) 4-tert-butyl phenoxide

Titanium (IV) 2,4-di-tert-butyl phenoxide

Titanium (IV) 2-tert-butyl-6-methyl phenoxide

Titanium (IV) 2,6-diisopropyl phenoxide

TABLE 1-continued

Ti-containing Compounds

Titanium (IV) 2,4-dicumyl phenoxide

Titanium (IV) 2-aminophenoxide

Titanium (IV) bis[2,2'-methylene-4,4'-dimethyl-6,6'-di-tert-butyl-bisphenolate]

Bis-1,3-phenylene-bis-3,3'-di-tert-butylphenl-2,2'-dioxytitanate

Bis(2-tert-butyl-6-methylphenoxy)-α,2-tolylenedioxytitanate

In certain embodiments, the second component contains an alcohol which is a diol or a mono-ol. Illustrative examples of diols include aliphatic diols, such as 1,3-propanediol, 2-methyl-1,3-propane diol, 1,4-butanediol, 1,5-pentanediol, 1,6-hexanediol, 1,7-heptanediol, 1,8-octanediol, 1,9-nonanediol, and 1,10-decanediol. Other diols include polyalkylene diols such as polyethylene diol, polypropylene diol, polybutylene diol, poly(ethylene-co-1, 2-butylene) diol, and poly(tetra-methylene ether) glycol. Still other diols include bis(2-hydroxyethyl) terephthalate and bis(2-hydroxybutyl) terephthalate. Illustrative examples of mono-ols include aliphatic mono-ols such as 1-propanol, 1-butanol, 1-pentanol, 1-hexanol, 1-heptanol, 1-octanol, 1-nonanol, 1-decyl alcohol, and polyalkylene mono-ols such as polyethylene mono-ol and polybutylene mono-ol.

In certain embodiments, the second component includes a triol, tetrol, or higher polyol. Illustrative examples of triols include trimethylolpropane, trimethylolethane, 3-methyl-1, 3,5-pentanetriol, and 1,3,6-hexanetriol. Examples of tetrols include ditrimethylolpropane and pentaerythritol. Examples of higher polyols include dipentaerythritol and tripentaerythritol. Examples of triols, tetrols, and higher polyols include polyalkylene triols, polyalkylene tetrols, and polyalkylene polyols, respectively.

In certain embodiments, the second component includes a monoepoxide, diepoxide, and/or a higher polyepoxide. Illustrative examples of monoepoxides include oxirane, 2-methyl oxirane, and 2,2-dimethyl oxirane. Examples of diepoxides include brominated bisphenol A diglycidyl ether, 1,2,7,8-diepoxyoctane, 1,3-butadiene diepoxide, and 1,2,5,6-diepoxyhexane.

Without wishing to be bound to any particular theory, it is believed that upon contact of an alcohol or an epoxide with a Ti-containing compound an exchange reaction occurs (e.g., transesterification reaction) resulting in a Ti-containing compound whose catalytic activity is greater due perhaps to a less sterically and/or electronically hindered Ti—O bond. It is possible to control the rate of reaction, the time required to initiate reaction, and the molecular weight of the polymerization product by varying reaction conditions. Reaction conditions include, for example, concentration of catalytic system components, relative molar ratio of catalytic system components, temperature, method of mixing, and reactant concentrations.

For example, one may vary the relative molar ratio of the catalytic system components in order to shorten the time required for initiation upon mixing of the catalytic components, or to affect the molecular weight of the product. In the case of multicomponent catalytic systems including a Ti-containing compound and an alcohol or epoxide, the molar amount of the alcohol or epoxide may be greater than the molar amount of the Ti-containing compound. These ratios may shorten the time required for initiation. It has also been noted that an excess amount of alcohol or epoxide may in certain circumstances affect the chain growth of a polymerization reaction, resulting in lower molecular weight polymeric products. Thus, depending on the desired results, molar ratios of Ti-containing compound to alcohol or epoxide can be selected from wide ranges. These ranges include, for example, 1:4–20 when a mono-ol is used, 1:2–10 when a diol or an epoxide is used, and 1:1.3–5 when a triol is used. It should be understood that other ranges of molar ratios of Ti-containing compound to alcohol or epoxide can also be used depending on implementation.

In certain embodiments, the catalytic system is capable of catalyzing the polymerization reaction of macrocyclic oligoester. Illustrative examples of macrocyclic oligoesters include macrocyclic oligoesters of ethylene terephthalate, 1,3-propylene terephthalate, 1,4-butylene terephthalate, 1,4-cyclohexylenedimethylene terephthalate, 1,2-ethylene 2,6-naphthalenedicarboxylate, and macrocyclic co-oligoesters based on two or more of the above or other monomer repeat units.

In certain embodiments, the first component of the catalytic system consists essentially of a Ti-containing compound, and the second component consists essentially of an alcohol or an epoxide. Alternatively, either or both of the first component and the second component may include one or more compounds other than a Ti-containing compound, an alcohol, or an epoxide. For example, either component may contain a filler, such as fumed silica, titanium dioxide, calcium carbonate, chopped fibers, fly ash, glass microspheres, micro-balloons, crushed stone, nanoclay, linear polymers and monomers, and combinations thereof. Any of these compounds may provide chemical, thermal, or light stability, weight or bulk, flame resistance, or other desirable properties as recognized by a skilled artisan. Also, either or both of the first component and the second component may include one or more additional compounds—including another Ti-containing compound, alcohol, epoxide, or an additive—to boost, inhibit, or otherwise affect catalytic activity.

In another aspect, the invention is directed to a method for polymerizing a macrocyclic oligoester. The method generally includes the steps of providing a first compound, providing a second compound, and contacting the first compound, the second compound, and a macrocyclic oligoester to polymerize the macrocyclic oligoester. The first compound and the second compound define at least part of a catalytic system, wherein the catalytic activity of the system increases upon contact of the first compound and the second compound in the presence of a macrocyclic oligoester. The catalytic system may include only the first compound and the second compound, or the catalytic system may include other catalyst compounds in addition to the first and second compounds. Examples of these other catalyst compounds include accelerators or other compounds which affect the rate of catalytic reaction.

Illustrative examples of macrocyclic oligoesters include macrocyclic oligoesters of ethylene terephthalate, 1,3-propylene terephthalate, 1,4-butylene terephthalate, 1,4-cyclohexylenedimethylene terephthalate, 1,2-ethylene 2,6-naphthalenedicarboxylate, and macrocyclic co-oligoesters based on two or more of the above or other monomer repeat units.

The step of contacting the first compound, the second compound, and a macrocyclic oligoester is typically performed at an elevated temperature. However, reaction conditions may be selected such that the reaction is carried out at ambient or lower temperatures. Typically, the macrocyclic oligoester is heated to above its melting point so it becomes less viscous and can be manipulated more easily in processing. This may occur before or during the contact of the first compound and the second compound in the presence of a macrocyclic oligoester. Subsequent to the contacting step, the temperature of the reacting mixture may be maintained or increased to initiate the polymerization reaction and/or speed the completion of the polymerization reaction. In some embodiments, the contacting step is conducted at a temperature within a range from about ambient temperature to about 260° C. In other embodiments, the contacting step is conducted at a temperature within a range from about 90° C. to about 260° C. In yet other embodiments, the contacting step is conducted at a temperature within a range from about 90° C. to about 200° C. Stirring may be employed under an inert atmosphere, such as under nitrogen or argon, in order to enhance polymerization of the macrocyclic oligoester to produce the desired polyester. Alternatively, stirring may be employed under air atmosphere.

In some embodiments, the step of contacting the first compound, the second compound, and a macrocyclic oligoester is conducted in a pre-mold mixer, which may include a mixing chamber. In one embodiment, each of the first compound, the second compound, and the macrocyclic oligoester is provided in the mixing chamber. The first compound, the second compound, and the macrocyclic oligoester are mixed in the mixing chamber, and are then subsequently introduced into a mold. In other embodiments, the step of contacting the first compound, the second compound, and a macrocyclic oligoester is conducted in a mold. In other embodiments, the step of contacting the first compound, the second compound, and a macrocyclic oligoester is conducted in an extruder.

In some embodiments, the first compound is a Ti-containing compound. In some embodiments, the Ti-containing compound has the molecular formula

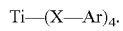
Ti—(X—Ar)$_4$.

Each X independently is O, S, or N. Each Ar group may independently be an organic group which includes an aromatic group. Alternatively, two or more Ar groups taken together may form an organic group which includes an aromatic group. The aromatic group is directly bonded to at least one X. The aromatic group may include a 5-membered ring, a 6-membered ring, and/or a 7- or higher-membered ring. The members of the ring may include carbon, or one or more heteroatoms such as S, N, or O, for example. The aromatic group may include one or more rings connected together in any configuration.

Illustrative examples of ring structures of the aromatic group include structures that are combinations of one or more 6-membered rings, such as structures comprising benzene, naphthalene, anthracene, phenanthrene, and chrysene. Other illustrative examples of ring structures of the aromatic group include aromatic heterocyclic structures, such as the structures comprising pyridine, furan, thiophene, pyrrole, and oxazole. Still other illustrative examples of ring structures of the aromatic group include monocyclics and polycyclics with a 5-membered ring, such as the structures comprising cyclopentadiene, indene, fluorene, indole, and purine.

In certain embodiments, each aromatic group independently is substituted at at least one ortho-position. In other embodiments, each aromatic group may be directly bonded to at least two X's, or each aromatic group is both substituted at at least one ortho-position and directly bonded to at least two X's. Illustrative substitution groups include alkyl groups and alkyl ether groups, which may be branched or unbranched, cyclic or acyclic, and substituted or unsubstituted. Illustrative examples of alkyl groups include methyl, ethyl, propyl, isopropyl, n-butyl, isobutyl, and pentyl groups. Illustrative examples of alkyl ether groups include diethyl ether, methyl-ethyl ether, methyl-n-propyl ether, methyl-isopropyl ether, and di-n-butyl ether groups. Other illustrative substitution groups include halogen, hydroxyl, carbonyl, and alkoxy groups.

In certain embodiments, each aromatic group independently is substituted with a bulky group at at least one ortho-position. Illustrative bulky groups include alkyl groups with two or more carbon atoms and alkyl ether groups, which may be branched or unbranched, cyclic or acyclic, and substituted or unsubstituted. Illustrative examples of bulky alkyl groups include is ethyl, propyl, isopropyl, n-butyl, isobutyl, and pentyl groups. Illustrative examples of bulky alkyl ether groups include diethyl ether, methyl-ethyl ether, methyl-n-propyl ether, methyl-isopropyl ether, and di-n-butyl ether groups. The bulky groups themselves may include halogen, hydroxyl, carbonyl, and alkoxy substitution groups. In certain embodiments, each aromatic group independently is substituted with a bulky group at two ortho-positions.

In certain embodiments, X is O such that the Ti-containing compound has the molecular formula

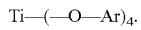
Ti—(—O—Ar)$_4$.

Ti-containing compounds that may be used in the invention include those listed in Table 1. In certain embodiments, at least one Ar group is not identical to the other Ar groups present in the Ti-containing compound. One such Ti-containing compound is bis(2-methyl-6-tert-butylphenoxy)-α, 2-tolylenedioxytitanate, seen in Table 1.

In certain embodiments, the second compound is an alcohol or an epoxide. Illustrative examples of diols include aliphatic diols, such as 1,3-propanediol, 2-methyl-1,3-propane diol, 1,4-butanediol, 1,5-pentanediol, 1,6-hexanediol, 1,7-heptanediol, 1,8-octanediol, 1,9-nonanediol, and 1,10-decanediol. Other diols include polyalkylene diols such as polyethylene diol, polypropylene diol, polybutylene diol, poly(ethylene-co-1,2-butylene) diol, and poly(tetra-methylene ether) glycol. Still other diols include bis(2-hydroxyethyl) terephthalate and bis(2-hydroxybutyl) terephthalate.

Illustrative examples of mono-ols include aliphatic mono-ols such as 1-propanol, 1-butanol, 1-pentanol, 1-hexanol, 1-heptanol, 1-octanol, 1-nonanol, 1-decyl alcohol, and polyalkylene mono-ols such as polyethylene mono-ol and polybutylene mono-ol.

In certain embodiments, the second compound is a triol, tetrol, or higher polyol. Illustrative examples of triols include trimethylolpropane, trimethylolethane, 3-methyl-1, 3,5-pentanetriol, and 1,3,6-hexanetriol. Examples of tetrols include ditrimethylolpropane and pentaerythritol. Examples of higher polyols include dipentaerythritol and tripentaerythritol. Examples of triols, tetrols, and higher polyols include polyalkylene triols, polyalkylene tetrols, and polyalkylene polyols, respectively.

In certain embodiments, the second compound is a monoepoxide, diepoxide, or a higher polyepoxide. Illustrative examples of monoepoxides include oxirane, 2-methyl oxirane, and 2,2-dimethyl oxirane. Examples of diepoxides include brominated bisphenol A diglycidyl ether, 1,2,7,8-diepoxyoctane, 1,3-butadiene diepoxide, and 1,2,5,6-diepoxyhexane.

In certain embodiments, either or each of the first compound and the second compound is provided along with a macrocyclic oligoester, forming two separate streams—the first compound being in the first stream, and the second compound being in the second stream. Each separate stream is relatively inactive over a period of time(i.e., possessing high melt stability), allowing sufficient time for mixing of either or each of the first compound and the second compound with the macrocyclic oligoester in their respective streams. The streams have high melt stability in that the molten macrocyclic oligoester in either or each stream does not polymerize to an appreciable extent for a period of time. Upon contact of the two streams, for example, inside a mold or a pre-mold mixer, the polymerization reaction may begin almost immediately because there is now contact between the first component and the second component in the presence of the macrocyclic oligoester. The polymerization of the macrocyclic oligoester may be complete within minutes.

In certain embodiments, the volume ratio of the first stream and the second stream is within a range from about 1:20 to about 20:1. In other embodiments, the volume ratio of the first stream and the second stream is within a range from about 1:3 to about 3:1.

In yet another aspect, the invention is directed to a method for making a co-polyester. The method generally includes the steps of providing a metal-containing compound, providing a diol having a molecular formula

$R(OH)_2$, and contacting the metal-containing compound and the diol in the presence of a macrocyclic oligoester, thereby producing a polyester having a structured unit of R, where R is an organic group. R may include an alkylene group, a polyether group, a polyalkylene group, and/or a co-polyalkylene group. R may be an alkylene group, which may be branched or unbranched, cyclic or acyclic, and substituted or unsubstituted. The alkylene group may contain substitution groups including halogen, hydroxyl, carbonyl, and alkoxy groups, for example. Illustrative examples of alkylene groups include ethylene, propylene, isopropylene, n-butylene, isobutylene, and is pentylene groups. R may also be a polyether group such as polytetramethylene ether. R may also be a polyalkylene group, such as polyethylene, polypropylene, polybutylene groups. R may also be a co-polyalkylene group. Illustrative examples of $R(OH)_2$ include aliphatic diols, such as 1,3-propanediol, 2-methyl-1,3-propane diol, 1,4-butanediol, 1,5-pentanediol, 1,6-hexanediol, 1,7-heptanediol, 1,8-octanediol, 1,9-nonanediol, and 1,10-decanediol. Other examples of $R(OH)_2$ include polyalkylene diols such as polyethylene diol, polypropylene diol, polybutylene diol, poly(ethylene-co-1,2-butylene) diol, and poly(tetra-methylene ether) glycol. Still other examples of $R(OH)_2$ include bis(2-hydroxyethyl) terephthalate and bis(2-hydroxybutyl) terephthalate.

In certain embodiments, the metal-containing compound has the molecular formula

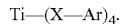
$Ti—(X—Ar)_4$.

Each X independently is O, S, or N. Each Ar group may independently be an organic group which includes an aromatic group. Alternatively, two or more Ar groups taken together may form an organic group which includes an aromatic group. Each Ar group may independently be an organic group which includes an aromatic group that is directly bonded to at least one X. Alternatively, two or more Ar groups taken together may form an organic group which includes an aromatic group that is directly bonded to at least one X.

In certain embodiments, X is O such that the metal-containing compound has the molecular formula

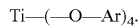
$Ti—(—O—Ar)_4$.

In certain embodiments, each aromatic group independently is substituted with a bulky group at at least one ortho-position. Additionally, each aromatic group may be directly bonded to at least two X's, or each aromatic group may be both substituted with a bulky group at at least one ortho-position and directly bonded to at least two X's.

Illustrative examples of the metal-containing compound are listed in Table 1.

The step of contacting the metal-containing compound, the diol or epoxide, and a macrocyclic oligoester may be performed at elevated temperatures or at ambient or lower temperatures. In certain embodiments, the contacting step is conducted at a temperature within a range from about ambient temperature to about 260° C. In other embodiments, the contacting step is conducted at a temperature within a range from about 90° C. to about 260° C. In yet other embodiments, the contacting step is conducted at a temperature within a range from about 90° C. to about 200° C.

II. Depolymerization of Polyester Using Aryl Titanate Catalysts

Depolymerization catalysts which are capable of producing macrocyclic oligoester from polyester are desired. It is further desired that macrocyclic oligoesters so produced be substantially free from impurities. It is also further desired that such depolymerization catalysts be soluble in the reaction solvent, be in a physical state which allows them to be readily added to the reaction mixture, and be capable of establishing the desired equilibrium between the macrocyclic oligoester and the polyester in a reasonable time under standard reaction conditions. Aryl titanate catalysts such as those described herein have been found to be useful in the depolymerization of polyesters and to satisfy these goals.

In one aspect, the invention relates to a method for depolymerizing a polyester that generally includes providing a polyester and providing a depolymerization catalyst that includes a compound with the molecular formula

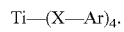
$Ti—(X—Ar)_4$.

Each X independently is O, S, or N. Each Ar group may independently be an organic group which includes an aromatic group. Alternatively, two or more Ar groups taken together may form an organic group which includes an aromatic group. Illustrative polyesters include polyethylene terephthalate, polybutylene terephthalate, and co-polyesters thereof. The polyester is contacted with the depolymerization catalyst. The polyester can be contacted with the depolymerization catalyst in the presence of a solvent. Illustrative examples of solvents include phenol, toluene, o-xylene, chlorobenzene, and o-dichlorobenzene.

Preferably, the polyester and the depolymerization catalyst are contacted at an elevated temperature. In certain embodiments, they are contacted at a temperature within a range from about ambient temperature to about 260° C. In other embodiments, they are contacted at a temperature within a range from about 90° C. to about 260° C. In yet other embodiments, they are contacted at a temperature within a range from about 90° C. to about 200° C.

III. Aryl-Titanate Catalysts

Certain aryl-titanate catalysts can be useful in both single-component and multi-component catalytic systems, particularly for polymerization of macrocyclic oligoesters and for depolymerization of polyesters, as discussed herein. These aryl titanate compounds may also be useful in esterification reactions and olefin polymerization. They may also be used in polymer cross-linking applications and in surface modification to control product properties.

In one aspect, the invention is directed to a catalyst that includes a Ti-containing compound having the molecular formula

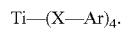
$Ti—(X—Ar)_4$.

Each X independently is O, S, or N. Each Ar group may independently be an organic group which includes an aromatic group that is directly bonded to at least one X. Alternatively, two or more Ar groups taken together may form an organic group which includes an aromatic group that is directly bonded to at least one X. Each aromatic group independently is substituted with a bulky group at at least one ortho-position, is directly bonded to at least two X's, or is both substituted with a bulky group at at least one ortho-position and is directly bonded to at least two X's.

The aromatic group may include a 5-membered ring, a 6-membered ring, and/or a 7- or higher-membered ring. The members of the ring may include carbon, or one or more heteroatoms such as S, N, or O, for instance. The aromatic group may include one or more rings connected together in any configuration. Illustrative examples of ring structures of the aromatic group include structures that are combinations of one or more 6-membered rings, such as structures comprising benzene, naphthalene, anthracene, phenanthrene, and chrysene. Other illustrative examples of ring structures of the aromatic group include aromatic heterocyclic structures, such as the structures comprising pyridine, furan, thiophene, pyrrole, and oxazole. Still other illustrative examples of ring structures of the aromatic group include monocyclics and polycyclics with a 5-membered ring, such as the structures comprising cyclopentadiene, indene, fluorene, indole, and purine.

In certain embodiments, each aromatic group independently is substituted with a bulky group at two ortho-positions. Illustrative bulky groups include alkyl groups with two or more carbon atoms and alkyl ether groups, which may be branched or unbranched, cyclic or acyclic, and substituted or unsubstituted. Illustrative examples of bulky alkyl groups include ethyl, propyl, isopropyl, n-butyl, isobutyl, and pentyl groups. Illustrative examples of bulky alkyl ether groups include diethyl ether, methyl-ethyl ether, methyl-n-propyl ether, methyl-isopropyl ether, and di-n-butyl ether groups. The bulky groups themselves may include halogen, hydroxyl, carbonyl, and alkoxy substitution groups.

In certain embodiments, X is O, such that the Ti-containing compound has the molecular formula Ti—(O—Ar)$_4$.

In certain embodiments, at least one Ar group is not identical to the other Ar groups present in the Ti-containing compound. In certain embodiments, each aromatic group independently is directly bonded to two X's. Illustrative examples of the Ti-containing compound are listed in Table 1.

In yet another aspect, the invention is directed to a method for polymerizing a macrocyclic oligoester using a single-component aryl titanate catalyst. The method generally includes providing a macrocyclic oligoester and providing a polymerization catalyst that includes a compound with the molecular formula Ti—(X—Ar)$_4$.

Each X independently is O, S, or N. Each Ar group may independently be an organic group which includes an aromatic group. Alternatively, two or more Ar groups taken together may form an organic group which includes an aromatic group. The macrocyclic oligoester is contacted with the polymerization catalyst.

In certain embodiments, the macrocyclic oligoester includes a macrocyclic oligoester of ethylene terephthalate, propylene terephthalate, 1,4-butylene terephthalate, or macrocyclic co-oligoesters thereof.

Preferably, the macrocyclic oligoester and the polymerization catalyst are contacted at an elevated temperature. However, reaction conditions may be selected such that the reaction is carried out at ambient or lower temperatures.

Typically, the macrocyclic oligoester is heated to above its melting point so it becomes less viscous and can be manipulated more easily in processing. This may occur before or during the contact of the macrocyclic oligoester with the polymerization catalyst. The temperature of the reacting mixture may be maintained or increased to initiate the polymerization reaction and/or increase the rate of the polymerization reaction.

In certain embodiments, the macrocyclic oligoester and the polymerization catalyst are contacted at a temperature within a range from about ambient temperature to about 260° C. In other embodiments, they are contacted at a temperature within a range from about 90° C. to about 260° C. In yet other embodiments, they are contacted at a temperature within a range from about 90° C. to about 200° C. Stirring may be employed under an inert atmosphere, such as under nitrogen or argon, in order to enhance polymerization of the macrocyclic oligoester to produce the desired polyester. Alternatively, stirring may be employed under air atmosphere.

In yet another aspect, the invention is directed to a composition including a macrocyclic oligoester and a compound having the molecular formula Ti—(X—Ar)$_4$.

Each X independently is O, S, or N. Each Ar group may independently be an organic group which includes an aromatic group. Alternatively, two or more Ar groups taken together may form an organic group which includes an aromatic group. In certain embodiments, the macrocyclic oligoester includes a macrocyclic oligoester of ethylene terephthalate, propylene terephthalate, 1,4-butylene terephthalate, or macrocyclic co-oligoesters thereof.

The composition may be used as a stream or as part of a stream in a multi-component catalytic system, wherein two or more co-catalysts are separated into two or more streams, which may contain reactant or other compounds. The composition is relatively inactive over a period of time, allowing sufficient time for mixing of the composition prior to exposure to the other stream(s), after which time appreciable reaction takes place.

In yet another aspect, the invention is directed to a catalyst that includes a compound having the molecular formula (R—Y$^1$—)$_i$-M-(—Y$^2$—Ar)$_j$.

Each of i and j are integers such that i≧0 and j≧1. The sum of i and j is either 4 or 6. Each Y$^1$ may independently be a single bond. Alternatively, each Y$^1$ may be a —O—(CH$_2$)$_x$— group where x is 1, 2, or 3, or a heteroatom selected from the group consisting of O, S, and N. Each Y$^2$ independently is O, S, or N. Each R group may independently be an alkyl group or an alkyl ether group. Alternatively, two or more R groups taken together may form an alkyl group or an alkyl ether group. The alkyl groups and the alkyl ether groups may be branched or unbranched, cyclic or acyclic, and substituted or unsubstituted. Each Ar group may independently be an organic group which includes an aromatic group that is directly bonded to at least one Y$^2$. Additionally, two or more Ar groups taken together may form an organic group which includes an aromatic group that is directly bonded to at least one Y$^2$. Each aromatic group independently is substituted with a bulky group at at least one ortho-position. M is either Ti or Sn.

Such a compound may be used in a multi-component catalytic system such as those discussed herein. In certain embodiments, i+j=4, each of Y$^1$ and Y$^2$ is O, and M is Ti, such that the compound has the molecular formula (R—O—)$_i$—Ti—(—O—Ar)$_j$.

EXAMPLES

The following non-limiting examples are provided to further illustrate and facilitate understanding of the invention. These specific examples are intended to be illustrative of the invention. The products obtained from these examples may be confirmed by conventional techniques such as proton and carbon-13 nuclear magnetic resonance spectroscopy, mass spectroscopy, infrared spectroscopy, differential scanning calorimetry, gel permeation chromatography, and other chromatographic analyses.

Preparation of Aryl Titanate Compounds

Example 1

A mixture of 30.0 grams (199.7 mmol) of 4-tert-butylphenol and approximately 100 mL of toluene was charged to a 200-mL three-neck round-bottom flask equipped with distillation adapter, a magnetic stirring bar, and a nitrogen inlet. The mixture was stirred and heated to reflux under nitrogen during which time approximately 20 mL of toluene was removed by distillation. The mixture was then cooled to about 100° C., and 13.47 grams (47.43 mmol) of tetra-isopropyl titanate was added to the mixture via a syringe. The mixture was heated and kept under reflux for an additional 30 minutes at about 160° C., and then isopropyl alcohol was removed by distillation at a distillation temperature within a range from about 85° C. to 90° C. After the liberation of isopropyl alcohol stopped, approximately 50 mL of liquid was removed by distillation at a temperature of about 140° C. The resulting dark red liquid was then cooled to room temperature. Upon cooling, the liquid crystallized yielding a red solid. After filtration, the red solid was dried overnight at 80° C. under vacuum. The yield was 29 grams, or about 94.8% of the theoretical maximum. The product is titanium (IV) 4-tert-butyl phenoxide, having the following formula:

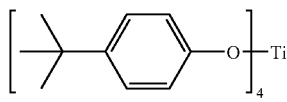

Example 2

A mixture of 30.0 grams (145.4 mmol) of 2,6-di-isopropylphenol and approximately 100 mL of toluene was charged to a 200-mL three-neck round-bottom flask equipped with distillation adapter, a magnetic stirring bar, and a nitrogen inlet. The mixture was stirred and heated to reflux under nitrogen during which time approximately 20 mL of toluene was removed by distillation. The mixture was then cooled to about 100° C., and 9.81 grams (34.53 mmol) of tetra-isopropyl titanate was added to the mixture via a syringe. The mixture was heated and kept under reflux for an additional 30 minutes at about 160° C., and then isopropyl alcohol was removed by distillation at a distillation temperature within a range from about 85° C. to 90° C. After the liberation of isopropyl alcohol stopped, approximately 50 mL of liquid was removed by distillation at a temperature of about 140° C. The resulting dark red, viscous liquid was then cooled to room temperature. Upon cooling, the liquid crystallized yielding a red solid. After filtration, the solid was dried overnight at 80° C. under vacuum. The yield was 30 grams, or about 99.8% of the theoretical maximum. The product is titanium (IV) 2,6-diisopropyl phenoxide, having the following formula:

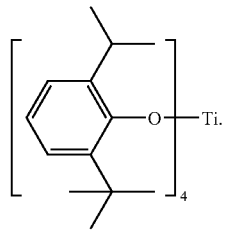

Example 3

A mixture of 40.3 grams (242.9 mmol) of 2-tert-butyl-6-methylphenol and approximately 100 mL of toluene was charged to a 200-mL three-neck round-bottom flask equipped with distillation adapter, a magnetic stirring bar, and a nitrogen inlet. The mixture was stirred and heated to reflux under nitrogen during which time approximately 20 mL of toluene was removed by distillation. The mixture was then cooled to about 100° C., and 16.38 grams (57.7 mmol) of tetra-isopropyl titanate was added to the mixture via a syringe. The mixture was heated and kept under reflux for an additional 30 minutes at about 190° C., and then isopropyl alcohol was removed by distillation at a distillation temperature within a range from about 85° C. to 90° C. After the liberation of isopropyl alcohol stopped, approximately 50 mL of liquid was removed by distillation at a temperature of about 140° C. The resulting dark red, viscous liquid was then cooled to room temperature. Upon cooling, the liquid crystallized yielding a red solid. After filtration, the red solid was dried overnight at 80° C. under vacuum. The yield was 39 grams, or about 96.4% of the theoretical maximum. The product is titanium (IV) 2-tert-butyl-6-methyl phenoxide, having the following formula:

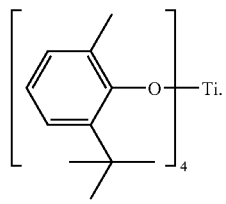

Example 4

A mixture of 40.0 grams (217.6 mmol) of 2,4-di-tert-butylphenol and approximately 100 mL of toluene was charged to a 200-mL three-neck round-bottom flask equipped with distillation adapter, a magnetic stirring bar, and a nitrogen inlet. The mixture was stirred and heated to reflux under nitrogen during which time approximately 20 mL of toluene was removed by distillation. The mixture was then cooled to about 100° C., and 14.7 grams (51.7 mmol) of tetra-isopropyl titanate was added to the mixture via a syringe. The mixture was heated and kept under reflux for an additional 30 minutes at about 160° C., and then isopropyl alcohol was removed by distillation at a distillation temperature within a range from about 85° C. to 90° C. After the liberation of isopropyl alcohol stopped, approximately 50 mL of liquid was removed by distillation at a temperature of about 140° C. The resulting red liquid was then cooled to room temperature. Upon cooling, the liquid crystallized yielding a needle-like solid. After filtration, the solid was dried overnight at 80° C. under vacuum. The yield was 38 grams, or about 97% of the theoretical maximum. The product is titanium (IV) 2,4-di-tert-butyl phenoxide, having the following formula:

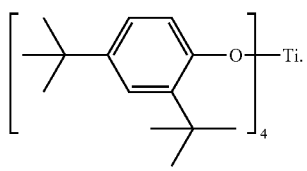

Example 5

A mixture of 60.0 grams (177.9 mmol) of 2,4-dicumylphenol and approximately 100 mL of toluene was charged to a 200-mL three-neck round-bottom flask equipped with distillation adapter, a magnetic stirring bar, and a nitrogen inlet. The mixture was stirred and heated to reflux under nitrogen during which time approximately 20 mL of toluene was removed by distillation. The mixture was then cooled to about 100° C., and 12.38 grams (34.59 mmol) of tetra-isopropyl titanate was added to the mixture via a syringe. The mixture was heated and kept under reflux for an additional 30 minutes at about 160° C., and then isopropyl alcohol was removed by distillation at a distillation temperature within a range from about 85° C. to 90° C. After the liberation of isopropyl alcohol stopped, approximately 50 mL of liquid was removed by distillation at a temperature of about 140° C. The resulting dark red, viscous liquid was then cooled to room temperature. Upon cooling, the liquid crystallized yielding a red solid. After filtration, the red solid was dried overnight at 80° C. under vacuum. The yield was 58 grams, or about 97.4% of the theoretical maximum. The product is titanium (IV) 2,4-dicumyl phenoxide, having the following formula:

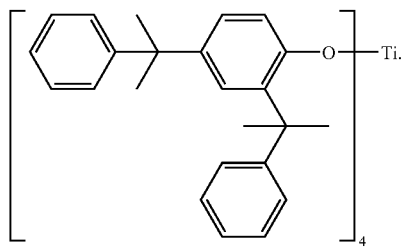

Example 6

A mixture of 20.0 grams (181.4 mmol) of 2-aminophenol and approximately 100 mL of toluene was charged to a 200-mL three-neck round-bottom flask equipped with distillation adapter, a magnetic stirring bar, and a nitrogen inlet. The mixture was stirred and heated to reflux under nitrogen during which time approximately 20 mL of toluene was removed by distillation. The mixture was then cooled to about 100° C., and 24.48 grams (86.18 mmol) of tetra-isopropyl titanate was added to the mixture via a syringe. The mixture was heated and kept under reflux for an additional 30 minutes at about 160° C., and then isopropyl alcohol was removed by distillation at a distillation temperature within a range from about 85° C. to 90° C. After the liberation of isopropyl alcohol stopped, approximately 50 mL of liquid was removed by distillation at a temperature of about 140° C. The resulting dark red, viscous liquid was then cooled to room temperature. Upon cooling, the liquid crystallized yielding a red solid. After filtration, the red solid was dried overnight at 80° C. under vacuum. The yield was 22 grams, or about 96.6% of the theoretical maximum. The product is titanium (IV) 2-aminophenoxide, having the following formula:

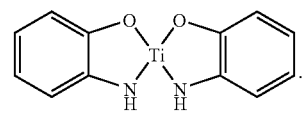

Example 7

A mixture of 25.0 grams (73.42 mmol) of 2,2'-methylene bis(6-tert-butyl-4-methylphenol) and approximately 100 mL of toluene was charged to a 200-mL three-neck round-bottom flask equipped with distillation adapter, a magnetic stirring bar, and a nitrogen inlet. The mixture was stirred and heated to reflux under nitrogen during which time approximately 20 mL of toluene was removed by distillation. The mixture was then cooled to about 100° C., and 10.22 grams (35.98 mmol) of tetra-isopropyl titanate was added to the mixture via a syringe. The mixture was heated and kept under reflux for an additional 30 minutes at about 160° C., and then isopropyl alcohol was removed by distillation at a distillation temperature within a range from about 85° C. to 90° C. After the liberation of isopropyl alcohol stopped, approximately 50 mL of liquid was removed at a temperature of about 140° C. The resulting dark red, viscous liquid was then cooled to room temperature. Upon cooling, the liquid crystallized yielding a red solid. After filtration, the red solid was dried overnight at 80° C. under vacuum. The yield was 25 grams, or about 95.8% of the theoretical maximum. The product is titanium (IV) bis[2,2'-methylene-4,4'-dimethyl-6,6'-di-tert-butyl-bisphenolate], having the following formula:

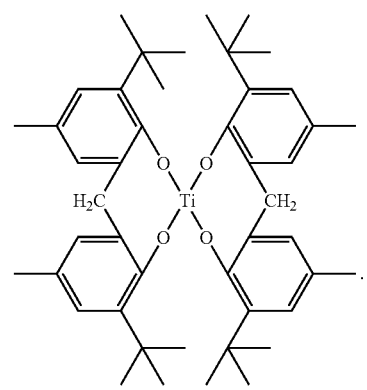

Example 8

A mixture of 31.64 grams (190.72 mmol) of 2-tert-butyl-6-methylphenol, 10.0 grams (90.82 mmol) of resorcinol, and approximately 100 mL of toluene was charged to a 200-mL three-neck round-bottom flask equipped with distillation adapter, a magnetic stirring bar, and a nitrogen inlet. The mixture was stirred and heated to reflux under nitrogen during which time approximately 20 mL of toluene was removed by distillation. The mixture was then cooled to about 100° C., and 25.79 grams (90.82 mmol) of tetra-isopropyl titanate was added to the mixture via a syringe. The mixture was heated and kept under reflux for an additional 30 minutes at about 160° C., and then isopropyl alcohol was removed by distillation at a distillation temperature within a range from about 85° C. to 90° C. After the liberation of isopropyl alcohol stopped, approximately 50 mL of liquid was removed by distillation under vacuum in an oil bath at a temperature of about 140° C. The resulting dark red, viscous liquid was then cooled to room temperature. Upon cooling, the liquid crystallized yielding a red solid. After filtration, the red solid was dried overnight at 80° C. under vacuumn. The yield was 43 grams, or about 98% of the theoretical maximum. The product is bis-1,3-phenylene-bis-3,3'-di-tert-butylphenl-2,2'-dioxytitanate, having the following formula:

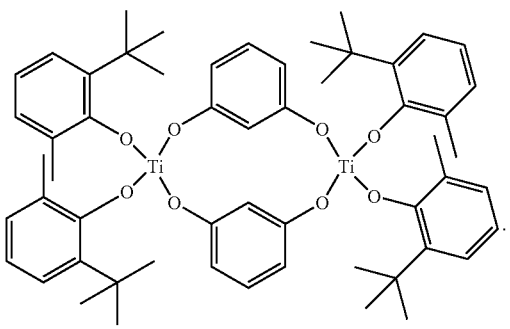

Example 9

A mixture of 5.0 grams (39.9 mmol) of 2-hydroxybenzyl alcohol, 13.2 grams (79.8 mmol) of 2-tert-butyl-6-methylphenol, and approximately 100 mL of toluene was charged to a 200-mL three-neck round-bottom flask equipped with distillation adapter, a magnetic stirring bar, and a nitrogen inlet. The mixture was stirred and heated to reflux under nitrogen during which time approximately 20 mL of toluene was removed by distillation. The mixture was then cooled to about 100° C., and 11.1 grams (39.1 mmol) of tetra-isopropyl titanate was added to the mixture via a syringe. The mixture was heated and kept under reflux for an additional 30 minutes at about 160° C., and then isopropyl alcohol was removed by distillation at a distillation temperature within a range from about 85° C. to 90° C. After the liberation of isopropyl alcohol stopped, approximately 50 mL of liquid was removed at a temperature of about 140° C. The resulting dark red, viscous liquid was then cooled to room temperature. Upon cooling, the liquid crystallized yielding a red solid. After filtration, the red solid was dried overnight at 80° C. under vacuum. The yield was 19 grams, or about 98% of the theoretical maximum. The product is bis(2-tert-butyl-6-methylphenoxy)-α,2-tolylenedioxytitanate, having the following formula:

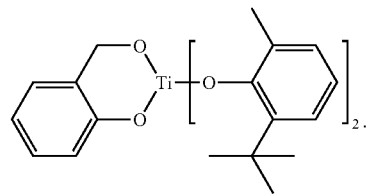

Polymerization of Macrocyclic Oligoesters Using Aryl Titanate Catalysts

Example 10

The macrocyclic oligoester used was macrocyclic co-oligoester having various degrees of oligomerization and containing about 95 mole percent of butylene terephthalate units and 5 mole percent of ethylene terephthalate units. A vial (21×70 mm, 4-drum) equipped with a magnetic stirring bar and a nitrogen/vacuum adapter was charged with 2.0 grams (8.91 mmol based on structural units) of the macrocyclic oligoester. The macrocyclic oligoester was dried by heating at approximately 190° C. at about 1 torr for about 5 minutes in an oil bath. The vacuum was released with nitrogen, and the temperature was maintained at approximately 190° C. Various quantities of polymerization catalyst were then added. A reaction timer was started at the time of catalyst addition. The time for the melt to stop the rotation of the magnetic stirring bar was noted as an indication of the induction period. After the stirring bar stopped rotating, heating under nitrogen was continued for about 15 minutes during which time the polymerized product began to crystallize, yielding a white solid. At the end of the polymerization, the vial was cooled to room temperature and broken to remove the polyester product, which was analyzed by gel permeation chromatography to determine percent polymerization and approximate weight average molecular weight relative to polystyrene. The results are shown in Table 2 along with a control polymerization wherein tetra-isopropyl titanate was the polymerization catalyst.

TABLE 2

Polymerization of Macrocyclic Oligoester Using Aryl Titanate Catalysts

| Catalyst | [Catalyst] Mole % | Induction Period, seconds[a] | Polymerization Time, minutes | Polymer Yield, % | Mw of Polymer |
|---|---|---|---|---|---|
| Control[b] | 0.30 | 5 | 15 | 97 | 20,000 |
| I | 0.30 | 20 | 15 | 86 | 119,000 |
| II | 0.30 | 150 | 16 | 67 | 155,000 |
| III | 0.30 | 1200 | 25 | 19 | 36,000 |
| IV | 0.30 | 630 | 15 | 6 | 33,000 |
| V | 0.60 | 240 | 32 | 68 | 124,000 |
| VI | 0.30 | 8580 | 143 | 0 | — |
| VII | 0.40 | 780 | 30 | 74 | 74,000 |
| VIII | 0.67 | 180 | 15 | 23 | 30,700 |
| IX | 0.60 | 405 | 30 | 30 | 142,700 |

[a]time required to stop rotation of stir bar
[b]tetra-isopropyl titanate.

Example 11

The polymerization procedure of Example 10 was followed to determine the melt stability of the macrocyclic oligoester from Example 10 in the presence of the compound produced in Example 3 at 150° C. and 190° C., using various concentrations of the compound. When a macrocyclic oligoester is used a reactant in a multicomponent catalytic system, it may be desirable to minimize polymerization of the macrocyclic oligoester in the presence of only one component of the catalytic system, in this case, titanium (IV) 2-methyl-6-tert-butyl phenoxide. Longer induction periods correspond to systems in which there are longer delays before significant polymerization begins, and, hence, higher melt stabilities. Table 3 shows the induction periods for various systems using the catalyst titanium (IV) 2-methyl-6-tert-butyl phenoxide at 150° C. and 190° C.

nent (e.g., a diol or an epoxide). The mixture of the macrocyclic oligoester and the diol or epoxide was dried by heating at approximately 190° C. at about 1 torr for about 5 minutes in an oil bath. The vacuum was released with nitrogen, and the temperature was maintained at approximately 190° C. The first component of the catalytic systems shown in Table 4 was then added. A reaction timer was started at the time of addition. The time for the melt to stop the rotation of the magnetic stirring bar was noted as an indication of the induction period. After the stirring bar stopped rotating, heating under nitrogen was continued for about 15 minutes during which time the polymerized prod-

TABLE 3

Polymerization of Macrocyclic Oligoester Using Titanium (IV) 2-tert-butyl-6-methyl phenoxide as Catalyst- Comparing Melt Stability

| Catalyst | [Catalyst] Mole % | Reaction Temperature, C. | Induction Period, seconds[a] | Polymerization Time, minutes | Polymer Yield, % | Mw of Polymer |
|---|---|---|---|---|---|---|
| Control[b] | 0.30 | 190 | 5 | 15 | 97 | 20,000 |
| III | 0.60 | 190 | 1140 | 30 | 38 | 29,800 |
| III | 0.60 | 150 | 1800 | 30 | 15 | 19,000 |
| III | 0.45 | 150 | 2580 | 45 | 13 | 20,700 |
| III | 0.40 | 150 | 2400 | 45 | 12 | 20,800 |
| III | 0.38 | 150 | 2580 | 45 | 11 | 20,200 |
| III | 0.30 | 150 | 2400 | 45 | 10 | 21,800 |

[a]time required to stop rotation of stir bar
[b]tetra-isopropyl titanate

Polymerization of Macrocyclic Oligoesters Using Two-Component Catalytic Systems

Example 12

A procedure similar to that of Example 10 was used for the polymerization of macrocyclic oligoester with a two-component catalytic system. The macrocyclic oligoester used was macrocyclic co-oligoester having various degrees of oligomerization and containing about 95 mole percent of butylene terephthalate units and 5 mole percent of ethylene terephthalate units. A vial (21×70 mm, 4-drum) equipped with a magnetic stirring bar and a nitrogen/vacuum adapter was charged with 2.0 grams (8.91 mmol based on structural units) of the macrocyclic oligoester and the second compouct began to crystallize, yielding a white solid. At the end of the polymerization, the vial was cooled to room temperature and broken to remove the polyester product, which was analyzed by gel permeation chromatography to determine percent polymerization and approximate weight average molecular weight relative to polystyrene. The results are shown in Table 4. A comparison of the example polymerizations of Table 3 with the example polymerizations of Table 4 involving titanium (IV) 2-methyl-6-tert-butyl phenoxide (compound III, as indicated in Table 4) shows that the two-component catalytic systems of Table 4 demonstrate much lower induction periods and produce polymer of much higher molecular weight than the comparable one-component catalytic systems of Table 3.

TABLE 4

Polymerization of Macrocyclic Oligoester Using Two-Component Catalytic Systems

| 1st Comp. | 1st Comp. conc., Mole % | 2nd Component | 2nd Component Concentration, Mole % | Induction Period, seconds[a] | Polymerization Time, minutes | Polymer Yield % | Mw of Polymer |
|---|---|---|---|---|---|---|---|
| II | 0.3 | Terathane 2900[b] | 0.6 | 10 | 16 | 95 | 112,900 |
| III | 0.3 | Poly(ethylene-co-1,2-butylene)diol[c] | 0.6 | 60 | 15 | 94 | 120,700 |
| III | 0.3 | Poly(ethylene-co-1,2-buthlene)diol | 6.5 | 60 | 15 | 99 | 21,200 |
| III | 0.3 | Brominated bisphenol A diglycidyl ether | 0.6 | 380 | 30 | 88 | 116,200 |
| III | 0.3 | Terathane 2900 | 0.6 | 12 | 15 | 84 | 120,700 |
| III | 0.3 | 1,4-Butanediol | 0.6 | 45 | 15 | 90 | 118,000 |
| III | 0.3 | 1,4-Butanediol | 1.2 | 15 | 15 | 95 | 115,400 |
| IV | 0.3 | Terathane 2900 | 0.6 | 11 | 15 | 90 | 107,000 |
| V | 0.3 | Terathane 2900 | 0.6 | 10 | 15 | 90 | 114,600 |
| VII | 0.2 | Terathane 2900 | 0.6 | 170 | 30 | 95 | 109,800 |

TABLE 4-continued

Polymerization of Macrocyclic Oligoester Using Two-Component Catalytic Systems

| 1st Comp. | 1st Comp. conc., Mole % | 2nd Component | 2nd Component Concentration, Mole % | Induction Period, seconds[a] | Polymerization Time, minutes | Polymer Yield % | Mw of Polymer |
|---|---|---|---|---|---|---|---|
| VIII | 0.3 | Terathane 2900 | 0.6 | 20 | 60 | 76 | 120,000 |
| VIII | 0.3 | Terathane 2900 | 1.2 | 15 | 15 | 98 | 70,400 |
| IX | 0.3 | Terathane 2900 | 0.6 | 110 | 30 | 68 | 83,100 |

[a]time required to stop rotation of stir bar;
[b]DuPont product, Polytetramethyleneether glycol with number average molecular weight Mn of 2900;
[c]number average molecular weight Mn of 3400

Depolymerization of Polyester in Preparation of Macrocyclic Oligoesters

Example 13

Polybutylene terephthalate oligoester was prepared by dissolving polybutylene terephthalate polymer pellets (1.81 g Valox 315) in o-dichlorobenzene (173.8 g) at approximately 180° C. in a 250-mL, 3-necked flask. The flask was equipped with a mechanical stirrer, a short path distillation head and receiver, and a Claisen head fitted with a thermometer and an inert gas inlet. Distillate (22 g) was removed overhead to dry the solution. Tetra-phenoxy titanate was prepared by condensation of 4 moles of phenol with 1 mole of tetra-isopropyl titanate. Tetra-phenoxy titanate, the depolymerization catalyst, was added at 1.75 mol% versus polybutylene terephthalate, and after about 2 hours at approximately 180° C. a 44% yield of polybutylene terephthalate macrocyclic oligoesters was measured by HPLC. Diol peaks typically observed in reaction mixtures prepared at 180° C. using other, non-aryl titanate catalysts were not observed. The reaction product was allowed to cool to room temperature and was filtered to remove precipitated linear polyester. The filtrate containing the macrocyclic oligoester was concentrated to dryness.

The crude macrocyclic oligoester product was compounded with the polymerization catalyst, 0.4 mol % Fascat 4101 (butyltin chloride dihydroxide, commercially available from Atofina). The macrocyclic oligoester polymerized to a weight average molecular weight of 158,000 Mw at approximately 190° C. for about 30 minutes.

What is claimed is:

1. A catalyst comprising a Ti-containing compound having the molecular formula

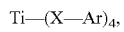

wherein each X independently is O, S, or N, and each Ar group independently is an organic group and comprises, or two or more Ar groups taken together form an organic group which comprises, an aromatic group directly bonded to at least one X, wherein each aromatic group independently is substituted with a bulky group at at least one ortho-position, is directly bonded to at least two X's, or both.

2. The catalyst of claim 1 wherein X is O.

3. The catalyst of claim 1 wherein at least one Ar group is not identical to the other Ar groups.

4. The catalyst of claim 1 wherein each aromatic group independently is substituted with a bulky group at two ortho-positions.

5. The catalyst of claim 1 wherein each aromatic group independently is directly bonded to two X's.

6. The catalyst of claim 2 wherein the Ti-containing compound is selected from the group consisting of titanium (IV) 4-tert-butyl phenoxide, titanium (IV) 2,4-di-tert-butyl phenoxide, titanium (IV) 2-methyl-6-tert-butyl phenoxide, titanium (IV) 2,6-diisopropyl phenoxide, and titanium (IV) 2,4-dicumyl phenoxide.

7. The catalyst of claim 1 wherein the Ti-containing compound is selected from the group consisting of

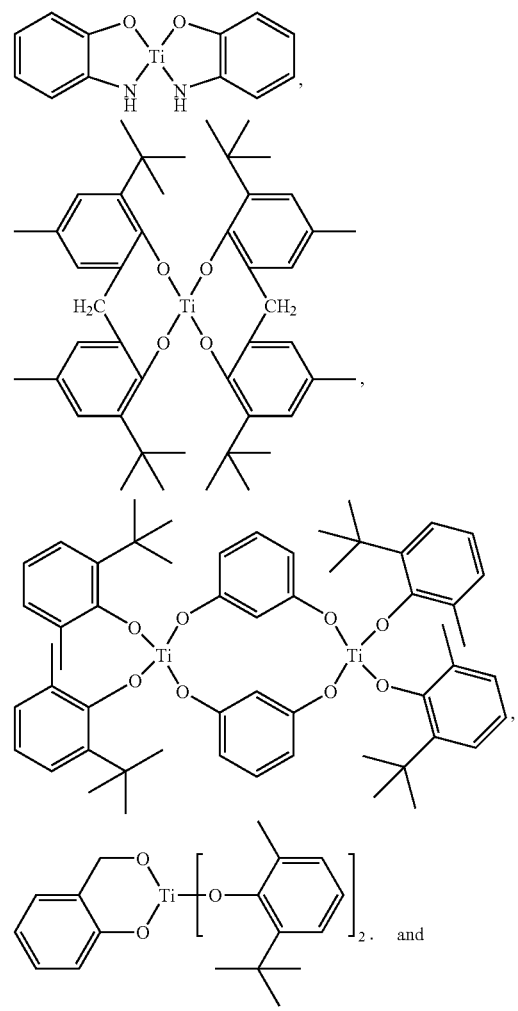

8. A composition comprising:
(a) a macro cyclic oligoester comprising a structural repeat unit of the formula

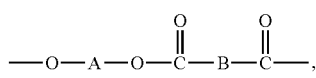

where A is an alkylene, a cycloalkylene, or a mono- or polyoxyalkylene group; and B is a divalent aromatic or alicyclic group; and (b) a compound having the molecular formula Ti—(X—Ar)$_4$, wherein each X independently is O, S, or N, and each Ar group independently is an organic group and comprises, or two or more Ar groups taken together form an organic group which comprises, an aromatic group that is directly bonded to at least one X.

9. The composition of claim 8 wherein X is O, and the macrocyclic oligoester comprises a macrocyclic oligoester of ethylene terephthalate, 1,4-butylene terephthalate, or both.

10. The composition of claim 8 wherein each aromatic group in the compound (b) independently is substituted with a bulky group at at least one ortho-position, is directly bonded to at least two X's, or both.

11. The composition of claim 8 wherein each aromatic group in the compound (b) independently is substituted with a bulky group at at least one ortho-position.

12. The composition of claim 8 wherein each aromatic group in the compound (b) is directly bonded to at least two X's.

13. The composition of claim 8 wherein the compound (b) is selected from the group consisting of titanium (IV) 4-tert-butyl phenoxide, titanium (IV) 2,4-di-tert-butyl phenoxide, titanium (IV) 2-methyl-6-tert-butyl phenoxide, titanium (IV) 2,6-diisopropyl phenoxide, and titanium (IV) 2,4-dicumyl phenoxide.

14. The composition of claim 8 wherein the compound (b) is selected from the group consisting of

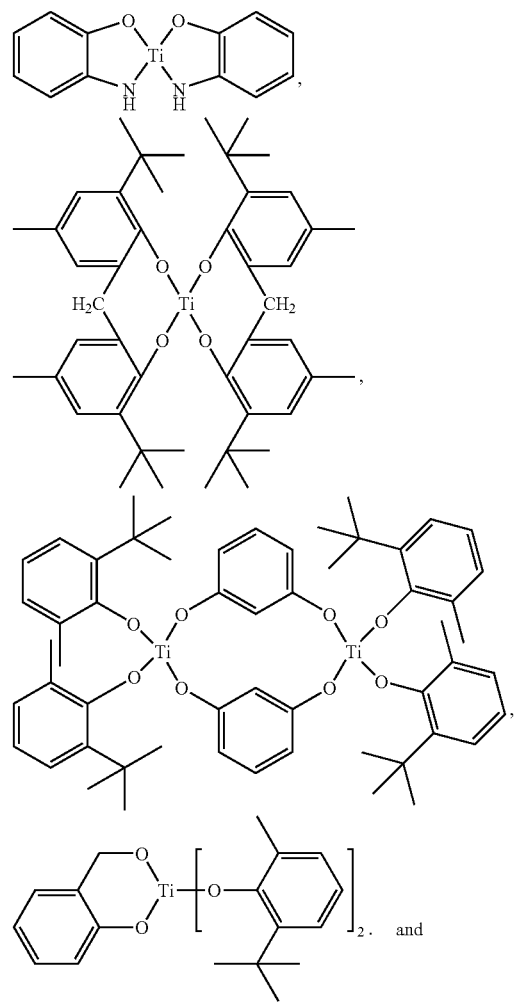

* * * * *

UNITED STATES PATENT AND TRADEMARK OFFICE
CERTIFICATE OF CORRECTION

PATENT NO. : 7,186,666 B2
APPLICATION NO. : 11/091,721
DATED : March 6, 2007
INVENTOR(S) : Yi-Feng Wang et al.

It is certified that error appears in the above-identified patent and that said Letters Patent is hereby corrected as shown below:

Column 28, line 61, replace "macro cyclic" with --macrocyclic--.

Signed and Sealed this

Twenty-fifth Day of December, 2007

JON W. DUDAS
*Director of the United States Patent and Trademark Office*